(12) United States Patent
Webb et al.

(10) Patent No.: US 7,988,688 B2
(45) Date of Patent: Aug. 2, 2011

(54) MINIATURE APPARATUS AND METHOD FOR OPTICAL STIMULATION OF NERVES AND OTHER ANIMAL TISSUE

(75) Inventors: James S. Webb, Seattle, WA (US);
Charles I. Miyake, Kirkland, WA (US);
Mark P. Bendett, Kirkland, WA (US);
Charles A. Lemaire, Apple Valley, MN (US)

(73) Assignee: Lockheed Martin Corporation, Bethesda, MD (US)

( * ) Notice: Subject to any disclaimer, the term of this patent is extended or adjusted under 35 U.S.C. 154(b) by 1312 days.

(21) Appl. No.: 11/536,639

(22) Filed: Sep. 28, 2006

(65) Prior Publication Data

US 2008/0077198 A1 Mar. 27, 2008

Related U.S. Application Data

(60) Provisional application No. 60/826,538, filed on Sep. 21, 2006.

(51) Int. Cl.
*A61N 5/06* (2006.01)
(52) U.S. Cl. .............................. 606/13; 607/89; 128/898
(58) Field of Classification Search .............. 607/88–94; 128/898
See application file for complete search history.

(56) References Cited

U.S. PATENT DOCUMENTS

| | | |
|---|---|---|
| 4,064,872 A | 12/1977 | Caplan |
| 4,232,678 A | 11/1980 | Skovajsa |
| 4,296,995 A | 10/1981 | Bickel |
| 4,558,703 A | 12/1985 | Mark |
| 4,681,791 A | 7/1987 | Shibahashi et al. |
| 4,768,516 A | 9/1988 | Stoddart et al. |

(Continued)

FOREIGN PATENT DOCUMENTS

WO WO0025112 5/2000

OTHER PUBLICATIONS

Maiorov, M., et al., "218 W quasi-CW operation of 1.83 um two-dimensional laser diode array", "Electronics Letters", Apr. 15, 1999, pp. 636-638, vol. 35, No. 8.

(Continued)

*Primary Examiner* — Henry M Johnson, III
*Assistant Examiner* — Jeffrey B Lipitz
(74) *Attorney, Agent, or Firm* — Charles A. Lemaire; Jonathan M. Rixen; Lemaire Patent Law Firm, P.L.L.C.

(57) ABSTRACT

A hand-held self-contained nerve-stimulation device and method using light to provide a source of precise stimulation on one or more nerve fibers. In some embodiments, this simulation is provided through a device and method wherein a laser- or LED-light source is mounted to the handpiece. Light is passed from the light source through optical tip to simulate nerves. In some embodiments, the device is constructed from non-magnetic material such as glass, plastic or ceramics. In some embodiments, the light emanating from the optical tip can be controlled manually or automatically. In some embodiments, the handpiece contains a self-contained power source, such as batteries. In some embodiments, the handpiece is at least in part, activated by remote control in order to prevent moving the handpiece during activation. Some embodiments include a unit operable to sense a response of nerve stimulation and to suppress a laser-ablation surgery operation.

34 Claims, 10 Drawing Sheets

U.S. PATENT DOCUMENTS

| | | |
|---|---|---|
| 4,840,485 A | 6/1989 | Gratton |
| 4,928,695 A | 5/1990 | Goldman et al. |
| 4,972,331 A | 11/1990 | Chance |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,464,960 A | 11/1995 | Hall et al. |
| 5,480,482 A | 1/1996 | Novinson |
| 5,548,604 A | 8/1996 | Toepel |
| 5,553,614 A | 9/1996 | Chance |
| 5,564,417 A | 10/1996 | Chance |
| 5,664,574 A | 9/1997 | Chance |
| 5,704,899 A | 1/1998 | Milo |
| 5,792,051 A | 8/1998 | Chance |
| 5,796,889 A | 8/1998 | Xu et al. |
| 5,899,865 A | 5/1999 | Chance |
| 6,110,195 A | 8/2000 | Xie et al. |
| 6,152,882 A | 11/2000 | Prutchi |
| 6,184,542 B1 | 2/2001 | Alphonse |
| 6,224,969 B1 | 5/2001 | Steenbergen et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,314,324 B1 | 11/2001 | Lattner et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,444,313 B1 | 9/2002 | Ono et al. |
| 6,459,715 B1 | 10/2002 | Khalfin et al. |
| 6,475,800 B1 | 11/2002 | Hazen et al. |
| 6,493,476 B2 | 12/2002 | Bendett |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,744,548 B2 | 6/2004 | Abeles |
| 6,748,275 B2 | 6/2004 | Lattner et al. |
| RE038,670 E | 12/2004 | Asah et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,956,650 B2 | 10/2005 | Boas et al. |
| 6,989,023 B2 | 1/2006 | Black |
| 7,004,645 B2 | 2/2006 | Lemoff et al. |
| 7,006,749 B2 | 2/2006 | Illich et al. |
| 7,031,363 B2 | 4/2006 | Biard et al. |
| 7,040,805 B1 | 5/2006 | Ou et al. |
| 7,116,886 B2 | 10/2006 | Colgan et al. |
| 7,139,603 B2 | 11/2006 | Chance |
| 7,225,028 B2 | 5/2007 | Della Santina et al. |
| 7,244,253 B2 | 7/2007 | Neev |
| 7,302,296 B1 | 11/2007 | Hoffer |
| 7,391,561 B2 | 6/2008 | Di Teodoro et al. |
| 2002/0002391 A1* | 1/2002 | Gerdes ........................... 607/89 |
| 2002/0123781 A1 | 9/2002 | Shanks et al. |
| 2002/0147400 A1 | 10/2002 | Chance |
| 2003/0083724 A1 | 5/2003 | Jog et al. |
| 2003/0232303 A1* | 12/2003 | Black ............................. 433/29 |
| 2003/0236458 A1 | 12/2003 | Hochman |
| 2004/0073101 A1 | 4/2004 | Chance |
| 2004/0116985 A1 | 6/2004 | Black |
| 2004/0225339 A1 | 11/2004 | Yaroslaysky et al. |
| 2004/0243111 A1 | 12/2004 | Bendett et al. |
| 2004/0243112 A1 | 12/2004 | Bendett et al. |
| 2005/0065531 A1 | 3/2005 | Cohen |
| 2005/0096720 A1 | 5/2005 | Sharma et al. |
| 2005/0099824 A1 | 5/2005 | Dowling et al. |
| 2005/0131499 A1* | 6/2005 | Shanks et al. ................. 607/89 |
| 2005/0142344 A1 | 6/2005 | Toepel |
| 2005/0169597 A1 | 8/2005 | Colgan et al. |
| 2005/0228256 A1 | 10/2005 | Labadie et al. |
| 2006/0095105 A1 | 5/2006 | Jog et al. |
| 2006/0129210 A1 | 6/2006 | Cantin et al. |
| 2006/0161218 A1 | 7/2006 | Danilov |
| 2006/0161227 A1 | 7/2006 | Walsh et al. |
| 2007/0053996 A1 | 3/2007 | Boyden et al. |
| 2007/0054319 A1 | 3/2007 | Boyden et al. |
| 2007/0060983 A1 | 3/2007 | Merfeld |
| 2007/0060984 A1 | 3/2007 | Webb et al. |
| 2007/0179557 A1 | 8/2007 | Maschino et al. |
| 2007/0261127 A1 | 11/2007 | Boyden et al. |
| 2008/0009748 A1 | 1/2008 | Gratton et al. |
| 2008/0077198 A1 | 3/2008 | Webb et al. |
| 2008/0077200 A1 | 3/2008 | Bendett et al. |
| 2008/0086206 A1 | 4/2008 | Nasiatka et al. |
| 2008/0140149 A1 | 6/2008 | John et al. |
| 2008/0161697 A1 | 7/2008 | Chance |
| 2009/0030327 A1 | 1/2009 | Chance |
| 2009/0163982 A1 | 6/2009 | DeCharms |
| 2009/0177255 A1 | 7/2009 | Merfeld |
| 2010/0114095 A1* | 5/2010 | Janssen et al. ................. 606/41 |

OTHER PUBLICATIONS

Nakagawa Atsuhiro, et al., "Pulsed holmium:yttrium-aluminum-garnet laser-induced liquid jet as a novel dissection device in neuroendoscopic surgery", "J. Neurosurg.", Jul. 2004, pp. 145-150, vol. 101.

Princeton Lightwave, "High Power Multimode Laser Arrays", "www.princetonlightwave.com/content/pli_high_power_multimode_laser_arrays.pdf", 2005.

Princeton Lightwave, "High Power Water Cooled Laser Stack", "www.princetonlightwave.com", 2005.

Princeton Lightwave, "High Power Single Element Laser," " www.princetonlightwave.com/content/HP%20Single%20Element%20Laser%20version%202.pdf", 2005.

Allegre, et al., "Stimulation in the rat of a nerve fiber bundle by a short UV pulse from an excimer laser", "NeuroScience Letters", 1994, pp. 261-264, vol. 180.

Fork, Richard L., "Laser Stimulation of Nerve Cells in Aplysia", "Science, New Series", Mar. 5, 1971, pp. 907-908, vol. 171, No. 3974.

Arridge et al., "The theoretical basis for the determination of optical pathlengths in tissue: temporal and frequency analysis", "Phys. Med. Biol.", 1992, pp. 1531-1560, vol. 37.

Chance et al., "Comparison of time-resolved and -unresolved measurements of deoxyhemoglobin in brain", "Proc. Nati. Acad. Sci. USA", Jul. 1988, pp. 4971-4975, vol. 85.

Desmurget et al, "Movement Intention after Parietal Cortex Stimulation in Humans", "Science", May 8, 2009, pp. 811-813, vol. 324.

Haggard, "The Sources of Human Volition", "Science", May 8, 2009, pp. 731-733, vol. 324.

Passos, D., et al., "Tissue phantom for optical diagnostics based on a suspension of microspheres with a fractal size distribution", "Journal of Biomedical Optics.", Nov.-Dec. 2005, p. 064036, vol. 10, No. 6.

Rolfe, "In Vivo Near-Infrared Spectroscopy", "Annu. Rev. Biomed. Eng.", 2000, pp. 715-754, vol. 2.

Schwartz et al, "Auditory Brainstem Implants", "Neurotherapeutics: The Journal of the American Society for Experimental NeuroTherapeutics", Jan. 2008, pp. 128-136, vol. 5.

* cited by examiner

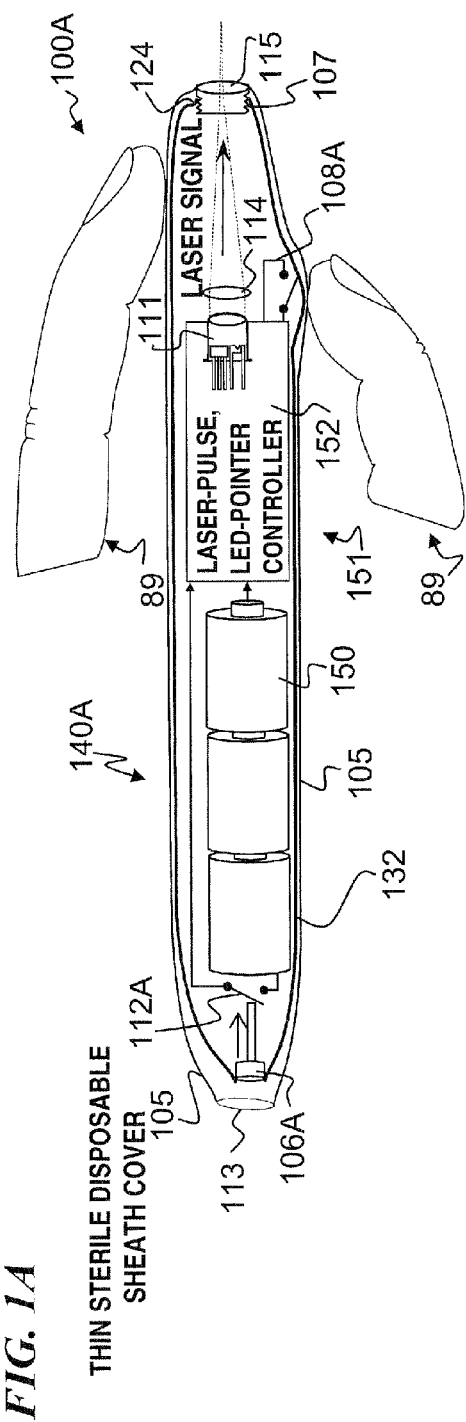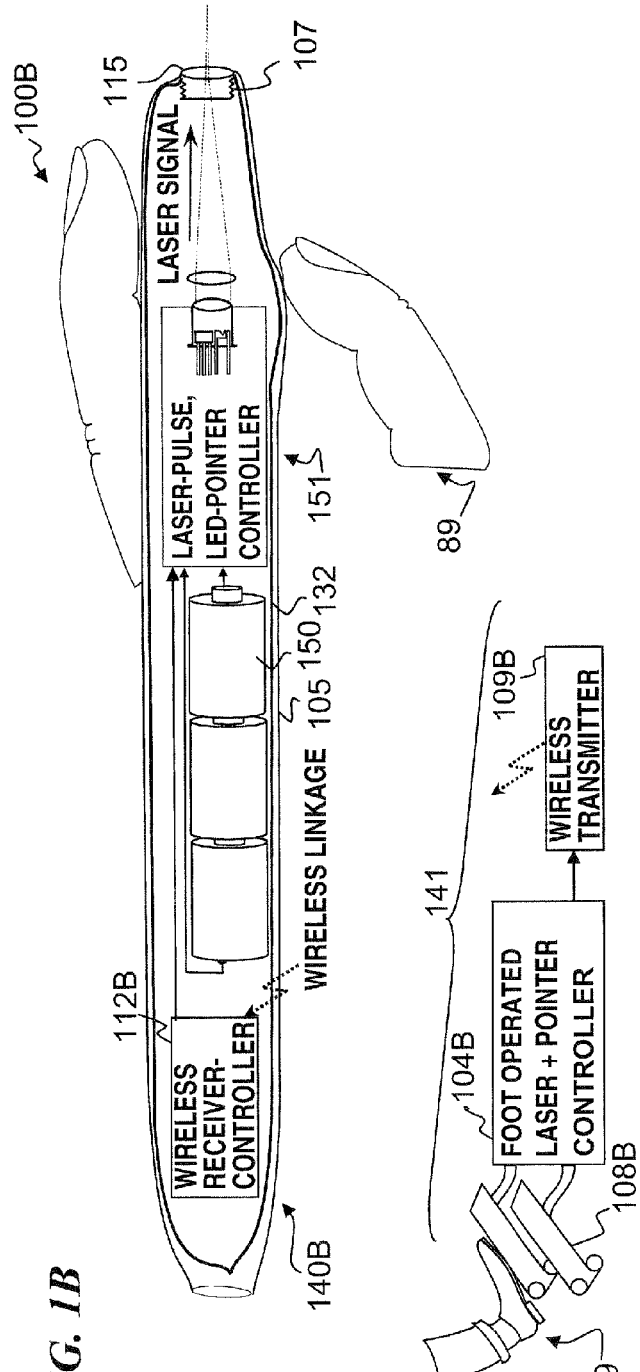
FIG. 1A
FIG. 1B

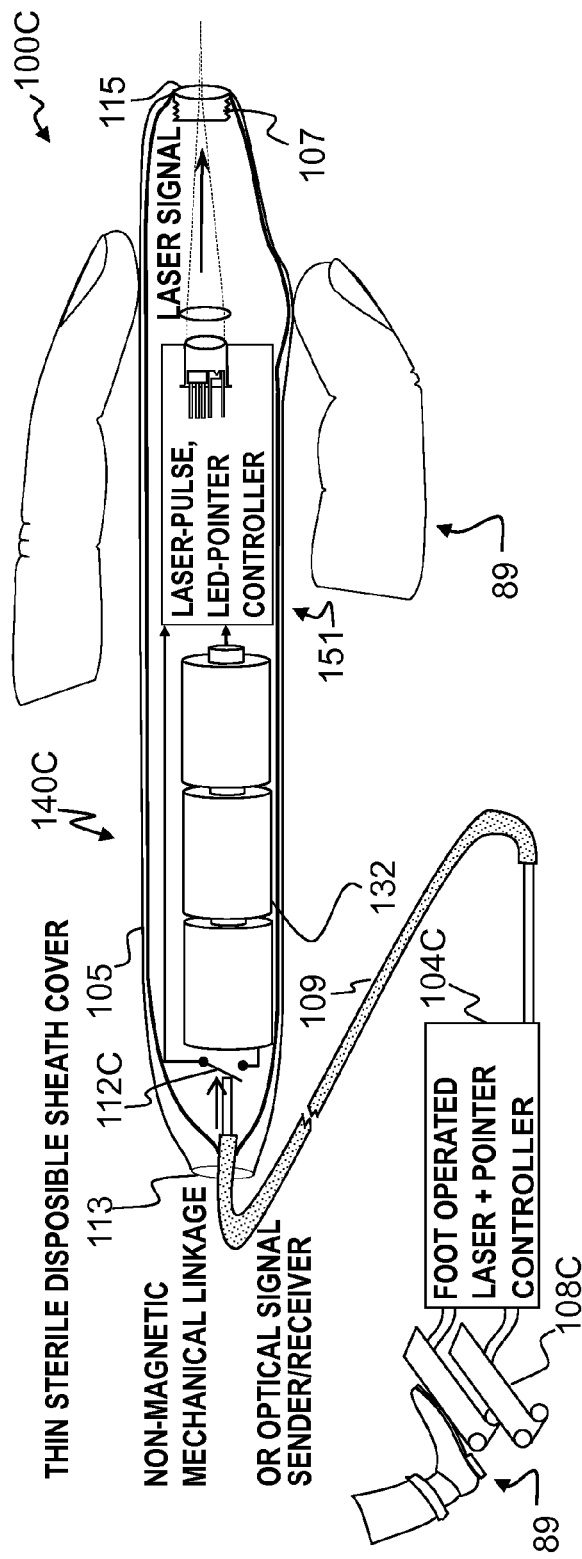
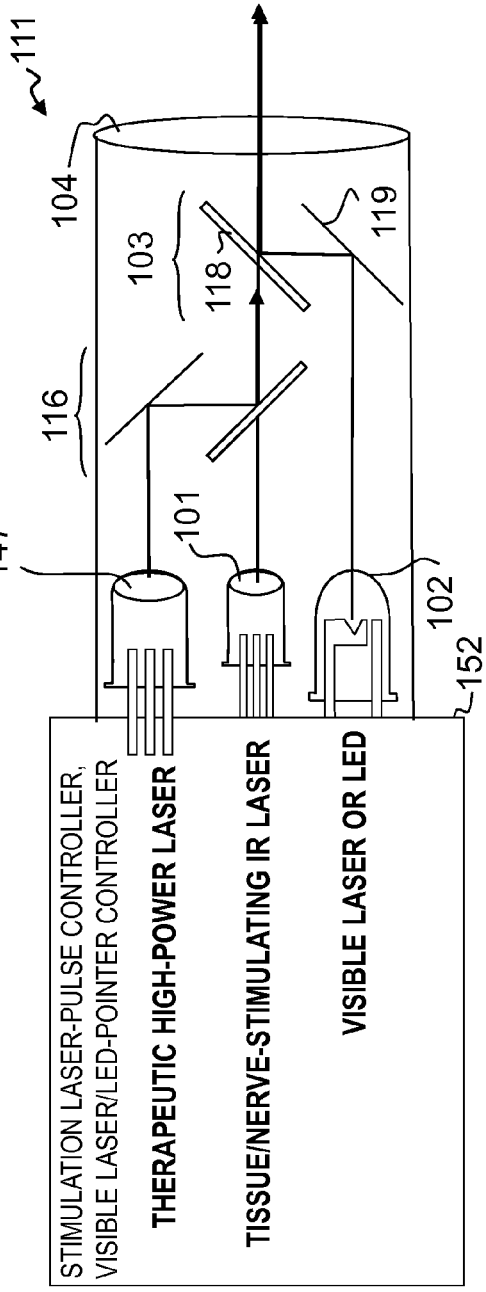

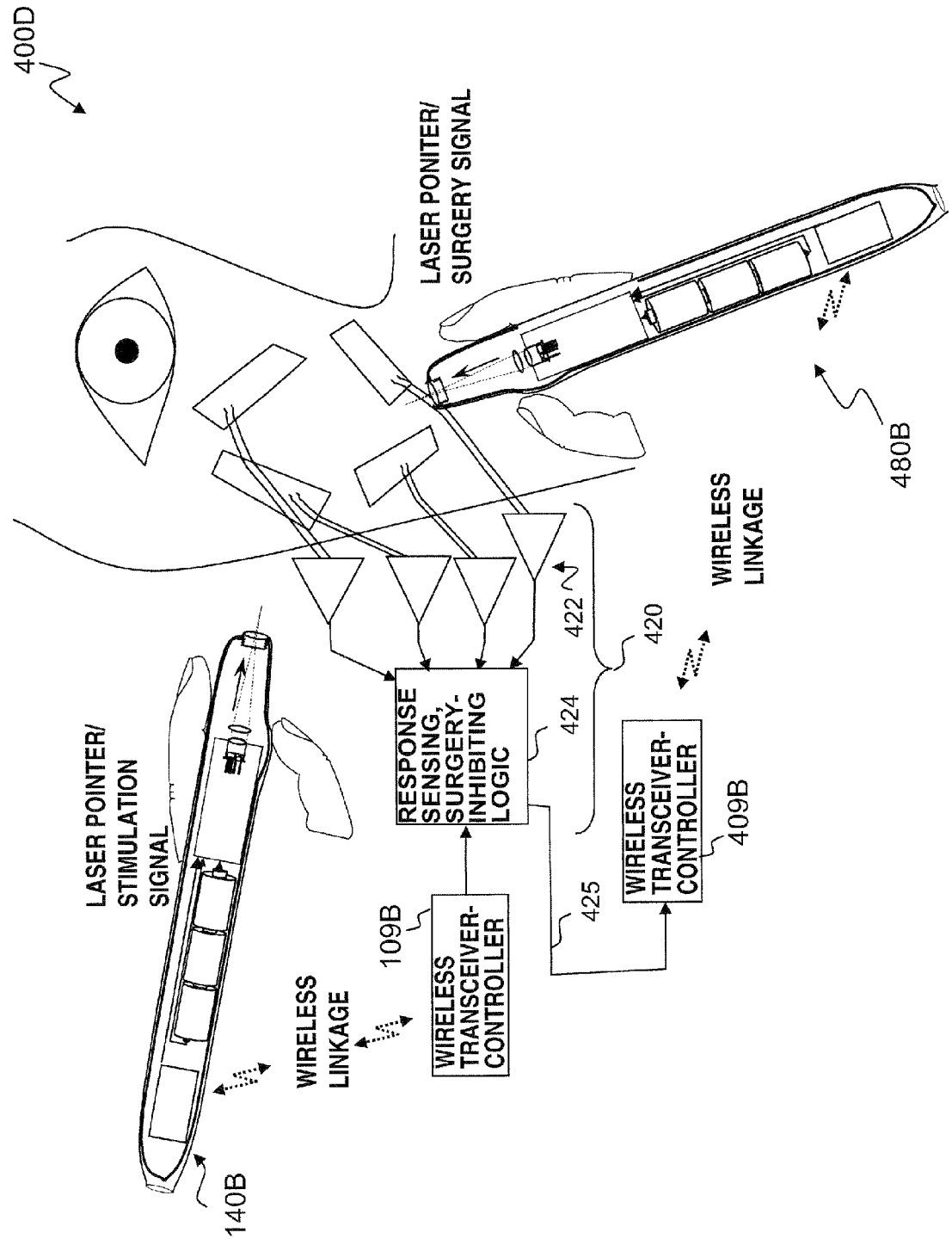

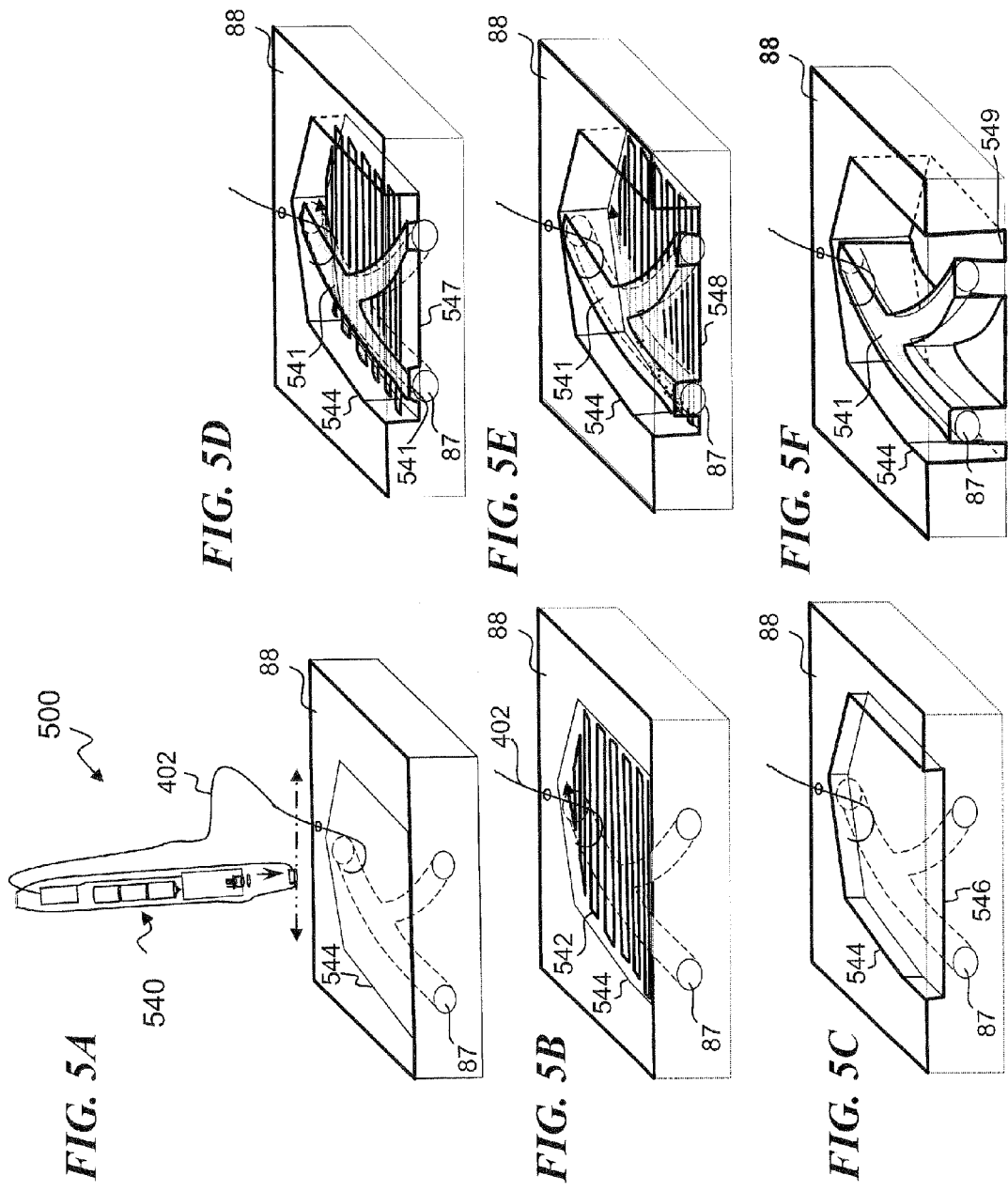

MINIATURE APPARATUS AND METHOD FOR OPTICAL STIMULATION OF NERVES AND OTHER ANIMAL TISSUE

CROSS-REFERENCE TO RELATED APPLICATIONS

This application claims benefit of U.S. Provisional Patent Application 60/826,538 filed on Sep. 21, 2006, titled "MINIATURE APPARATUS AND METHOD FOR OPTICAL STIMULATION OF NERVES AND OTHER ANIMAL TISSUE," which is incorporated herein by reference in its entirety. This application is also related to U.S. patent application Ser. No. 11/257,793 filed on Oct. 24, 2005 entitled "APPARATUS AND METHOD FOR OPTICAL STIMULATION OF NERVES AND OTHER ANIMAL TISSUE" (now U.S. Pat. No. 7,736,382 titled "APPARATUS FOR OPTICAL STIMULATION OF NERVES AND OTHER ANIMAL TISSUE"), and to U.S. patent application Ser. No. 11/536,642 filed on Sep. 28, 2006, entitled "APPARATUS AND METHOD FOR STIMULATION OF NERVES AND AUTOMATED CONTROL OF SURGICAL INSTRUMENTS," which are each incorporated herein by reference in their entirety.

FIELD OF THE INVENTION

The invention relates generally to optical nerve stimulation, and more particularly to methods and miniature and/or handheld apparatus to generate, direct, and control the optical signal used to stimulate nerves and other animal tissue, and in particular, neural tissue.

BACKGROUND OF THE INVENTION

A nerve can be stimulated in a number of different ways, including electrical, mechanical, thermal, chemical, and now optical. A nerve is a filament of neural tissue composed of cells each having a cell body and one or more axons and dendrites. The axons extend peripherally as either myelinated or unmyelinated fibers. A chain of Schwann cells surrounds each myelinated nerve fiber with a multilayered myelin sheath. Groups of unmyelinated fibers are associated with single Schwann cells. Both types of nerve fibers are bound by endoneurium to form bundles, or fascicles. A perineurial membrane surrounds each fascicle. Groups of fascicles are held together by internal and external epineurium to form the peripheral nerves. The cell body of a motor neuron lies in the anterior horn of the spinal cord, while the cell body of a sensory neuron is located in the dorsal root ganglion, near the cord. (Christine Cheng; See *Nerve Compression Syndromes of the Upper Limb*, by Martin Dunitz, published by Taylor & Francis Group, 2002.)

Functional magnetic-resonance-imaging (fMRI) systems use extremely strong magnetic fields in generating images of an animal subject (e.g., a human) to discern functions and abnormalities of various portions of the body, and in particular, of the brain (e.g., during various mental activities or thought patterns). The high static magnetic fields ($B_0$ fields) created by an MRI machine create a danger of projectile accidents from any object having magnetic properties that may be near the MRI machine. Using metal probes to deliver electrical stimulation to nerves of a subject poses one such danger. It would be desirable to stimulate a nerve without using metal probes.

Further, it is desirable to cause a controlled stimulation of individual nerves. U.S. Pat. No. 6,921,413 issued to Mahadevan-Jansen et al. on Jul. 26, 2005, and titled "Methods and Devices for Optical Stimulation of Neural Tissues," is incorporated herein by reference. Mahadevan-Jansen et al. note that traditional methods of stimulation include electrical, mechanical, thermal, and chemical. A neuron will propagate an electrical impulse (a nerve action potential) in response to a stimulus. The most common form of applying such stimulation is to form a transient current or voltage pulse applied through electrodes. Electrical, mechanical, and chemical stimulations have many limitations. Stimulation by such methods typically results in non-specific stimulation of neurons and/or damage to neurons. Difficulty exists in recording electrical activity from the neuron due to an electrical artifact created by the stimulus. To stimulate only one or a few neurons, fragile microelectrodes need to be fashioned and carefully inserted into the tissue to be stimulated. Such techniques do not easily lend themselves to implantable electrodes for long-term use in stimulation of neural tissue. Mahadevan-Jansen et al. describe the use of low-power light from a free-electron laser (FEL) for optically stimulating selected individual nerve cells in vivo, while at the same time not stimulating neighboring cells with the laser light. Unfortunately, FELs are expensive, large, awkward and unwieldy.

Further, some conventional optical systems include some magnetic materials, making them unsuitable for use near MRI systems.

In other conventional neural-stimulation systems, 110-volt AC (wall power) is used to control and/or drive the laser components, with electrical, cooling-fluid, and/or optical tethers between a delivery head and other portions of the equipment, making such systems clumsy and/or perhaps somewhat dangerous to use if relatively high voltages are present in the hand-held portion. For example, U.S. Pat. No. 5,548,604 issued to Toepel on Aug. 20, 1996 entitled "Compact hand held medical device laser" describes a palm-sized laser device having a hand-held housing containing a solid state crystal lase material rod, a flashlamp (for pulsed pump light) within a reflective light-coupling cavity and a fluid-cooling chamber adapted to receive and exhaust coolant fluid.

In view of shortcomings in such conventional devices, there is a need for devices and methods that can provide inexpensive, compact, optionally non-magnetic, optionally having non-wall-powered power supplies, and/or easy-to-use interfaces and form factors for optical stimulation of nerves.

BRIEF SUMMARY OF THE INVENTION

In some embodiments, the invention provides a method and self-powered (e.g., battery-powered) and/or hand-held apparatus for stimulating nerves using either an infra-red (IR) diode laser or light-emitting diode (LED) (e.g., one running at a wavelength of about 1.87 microns) or a diode-pumped solid-state laser (e.g., using a semiconductor laser diode as a pump source of optical radiation and an optically pumped semiconductor or optically pumped rare-earth-doped fiber laser cavity) running at a wavelength of 2.1 microns (e.g., a 785-micron-wavelength laser diode pumping a Tm/Ho solid-state crystal or fiber), or a laser diode operating at a wavelength of between about 1.8 and about 2.2 microns. In other embodiments, the invention uses other wavelengths that are efficacious in optical stimulation of animal tissue such as a nerve.

In some embodiments, the apparatus is at least mostly embedded in a self-contained hand-held form factor such as a light pen, pointer and/or wand that can be manually used to control, direct and/or shutter the light. In some embodiments, the hand-held device includes an embedded laser diode used to obtain optical radiation (optionally directed at least in part in an embedded optical fiber) that has a suitable wavelength and optical power sufficient to optically stimulate the nerve. In other embodiments, one or more LEDs, one or more diode lasers, or a combination of one or more LEDs and one or more diode lasers is used to obtain the stimulation light.

In some embodiments, the hand-held device of the present invention includes one or more internal power sources, such as battery cells, to provide self-contained electrical power to the laser diode and/or other internal components. In some embodiments, at least some of the metal portions of the battery and other internal electrical wiring connections are all or substantially all made of a non-magnetic electrically conductive material such as copper, in order to be usable near MRI equipment.

In some embodiments, one or more free-space or bulk optical components (such as air gaps, lenses, prisms and the like, in contrast to enclosing the entire optical path in optical fibers) are used in the hand-held device of the present invention. In some embodiments, one or more IR and/or visible lasers are implemented on a semiconductor chip, and one or more such chips are mounted to a housing (such as a metal or plastic "can" having a front lens) such that the combined optical output of the laser(s)/LED(s) starts in close proximity and is immediately collimated as a single beam and focussed by a single train of lenses and other optical components. In other embodiments, at least one beam-splitter/beam combiner is used to combine light from two or more sources into a single output beam.

In other embodiments, the IR nerve-stimulation optical signal is carried in an optical fiber, and, either sharing a single optical fiber or passing in one or more separate fibers next to the optical fiber that carries the IR nerve-stimulation optical signal, the invention also includes a visible-laser or visible-LED signal that illuminates and points out the area (e.g., the nerve) being stimulated. In still other embodiments, a high-power surgical and/or therapeutic laser signal is added in conjunction with the IR nerve-stimulation signal and/or visible pointer laser. For example, in some embodiments, a visible laser is projected to point out to the surgeon where the IR nerve-stimulation laser signal will be applied; the surgeon then activates the IR nerve-stimulation laser signal and observes the response (for example, phantom-limb pain of an amputee); and once the observed response determines the nerve location to be treated, the surgical and/or therapeutic laser signal is applied to that identified location. In other embodiments, for example to avoid accidentally cutting a facial nerve during surgery, the IR nerve-stimulation laser signal is pointed to a location that the surgeon wants to cut or ablate (in some embodiments, this point is illuminated by the visible pointer laser beam) but wants to cut only if no nerve is at that point; the surgeon then activates the IR nerve-stimulation laser signal and observes the response (for example, a muscle contraction that can be seen by the surgeon or sensed by a suitable sensor taped or otherwise affixed to the skin); but in this case, the observed response determines that a location to be treated includes a desired nerve, and the surgical and/or therapeutic laser signal is inhibited from being applied to that identified location. In some embodiments, the nerve-response sensor generates a signal that inhibits activation of the surgical laser.

The present invention, with its ability to precisely stimulate a single nerve or a very small area of a brain (optionally with no magnetic material near the subject, who, in some embodiments, may be a human patient requiring medical care) is a gateway technology that opens broad areas of medicine and surgery. In some embodiments, an enlarged digital or video image of the surgery site is displayed, and as the surgeon optically stimulates the various nerves or areas, the image is annotated (e.g., color-coded as a map of nerve function) to provide a record of which response was observed for each of the different areas stimulated. In some embodiments, once the annotated map is sufficiently complete, the surgeon can input graphical annotation to the computer identifying the extent or the exact area to which treatment is to be permitted, the visible signal (showing where the fiber is pointing) is inputted and compared to the map, such that the controller allows the surgical and/or therapeutic laser signal to be applied only to the identified allowed area.

As used herein, "optical stimulation of nerves" refers to stimulation caused by impinging light onto nerve tissue, regardless of the wavelength of the light (ultraviolet, visible, or infrared, wherein the term "light" is not necessarily restricted to light in the visible range of 400- to 700-nanometer wavelengths). The nerve being stimulated can be any nerve, such as motor or sensory nerves in the peripheral nervous system, nerve tissue of the central nervous system (nerves within the brain and spinal cord), the cranial nerves (e.g., the optic nerve, the olfactory nerve, the auditory nerve, and the like), optical or auditory nerves, the autonomic nervous system, as well as brain tissue and/or any other neural tissue. Thus, the tissue to which optical stimulation is applied need not itself be a "nerve" as conventionally defined, but could include brain tissue that when stimulated by light initiates a response similar to that carried by a nerve, e.g., an action potential that includes electrical and/or chemical components, and which is propagated to a location some distance from the point that was optically stimulated. As used herein, the term "subject" is an inclusive term that refers to any animal whose nerves may be stimulated by light, as the term light has been defined above; this includes non-mammalian and mammalian species, including humans, and including especially humans who may be patients receiving professional medical care. As used herein, the term "optical-fiber structure" is an inclusive term that includes a single optical fiber as well as a bundle of individual optical fibers, a fused bundle of optical fibers, star couplers, and depending on the context optionally includes ferrules, lenses, and the like used to couple light into and out of the optical fiber structure.

In some embodiments, the present invention includes at least some of the following in a small hand-held portable device powered by a self-contained energy-storage device (e.g., batteries or other power source, such as capacitors, chemical energy, rotational flywheel energy, spring energy and the like; and/or a self-contained power receiver such as a coil for receiving AC magnetic or RF energy, a photovoltaic cell for receiving optical energy, and the like), one or more light-emitting sources (that emit tissue-stimulation wavelengths) powered by the self-contained energy-storage device, an optional light-beam combiner coupled to combine two or more optical beams into a single optical beam, optics to focus and deliver light to a nerve, a trigger or activation mechanism, a light-emitting-source controller (e.g., in some embodiments, this includes electronics to condition and control electricity to laser diodes), one or more visible-light-emitting sources such as LEDs and/or laser diodes (that emit light used to point at or identify the tissue area being (or to be) stimulated and a disposable sheath. In some embodiments, the sheath includes or incorporates a lens and/or other portions of the optics to focus the light from the light sources to a particular spot size and/or shape. In some embodiments, a plurality of different interchangeable sheaths and/or lens tips are provided, each having a different spot size and/or shape, allowing the surgeon or technician to choose the appropriate light pattern, and/or to change the light pattern based on results of the first-tried sheath's light pattern and/or the patient response obtained.

In some embodiments, the invention provides a method that includes generating a first light beam from a first self-contained-energy-storage-powered (e.g., battery-powered) light-emitting source, generating a second light beam using a self-contained-energy-storage-powered (e.g., battery-powered) second light-emitting source, combining the first and second light beams, focusing the combined first and second laser light beams, and controlling an amplitude and/or timing of the first and/or second light beams.

In some embodiments, the present invention includes an apparatus having a finger-and/or-thumb control that controls a characteristic of light, optics to focus and deliver the light to a nerve, a self-contained-energy-storage-powered (e.g., battery-powered) laser having a wavelength and power capable of efficaciously stimulating a nerve, and a controller operable to drive the laser based on input from the finger/thumb control. In some embodiments, this apparatus is used to deliver an efficacious amount of visible and infrared (IR) light so as to target and stimulate nerve tissue. In some embodiments, a visible laser beam is used to point to and illuminate the area to be stimulated and an IR laser beam is used to stimulate a nerve at that illuminated area.

In some embodiments, the present invention includes an apparatus having an optical nerve stimulator, an energy-storage-device charger (e.g., battery charger), and a remote wireless controller and/or programmer.

In some embodiments, the stimulation light is IR (infrared, e.g., about 1.8-micron wavelength), while in other embodiments other IR wavelengths, visible light wavelengths, ultraviolet wavelengths, and/or combinations of a plurality of such wavelengths are used.

In some embodiments, the invention provides a method that includes charging a battery, (e.g., supplying a charge to a battery from an RF charger), powering a controller with the battery, powering a first light source from the controlled, powering a second light source, emitting light from the first light source, emitting light from the second light source, controlling a characteristic of the light from the first and second light sources using a remote programmer, combining the light from the first and second light sources via a combiner, and projecting the combined light to a nerve fiber.

BRIEF DESCRIPTION OF THE DRAWINGS

FIG. 1A is a block diagram of a battery-operated nerve-stimulation laser handpiece system 100A.

FIG. 1B is a block diagram of a battery-operated nerve-stimulation laser handpiece system 100B.

FIG. 1C is a block diagram of a battery-operated nerve-stimulation laser handpiece system 100C.

FIG. 1D is a block diagram of a battery-operated nerve-stimulation laser 111.

FIG. 4D is a block diagram of surgery-inhibiting nerve-stimulation system 400D.

FIG. 5A is a perspective cut-away diagram of a surgery-inhibiting nerve-stimulation system at the initiation of a surgical procedure.

FIG. 5B is a diagram of a first stimulation/surgical pattern at an operation site at which a surgery-inhibiting nerve-stimulation system is employed, at a first time subsequent to the initiation of a surgical procedure.

FIG. 5C is a diagram of a surgical site at which a surgery-inhibiting nerve-stimulation system is employed, at a time when the stimulation/surgical pattern shown in FIG. 5B has been completed.

FIG. 5D is a diagram of a second stimulation/surgical pattern at an operation site at which a surgery-inhibiting nerve-stimulation system is employed, at a second, later time subsequent to the initiation of a surgical procedure, and showing the surgical site at a time when the second stimulation/surgical pattern has been completed.

FIG. 5E is a diagram of a third stimulation/surgical pattern at an operation site at which a surgery-inhibiting nerve-stimulation system is employed, at a third, later time subsequent to the initiation of a surgical procedure, and showing the surgical site at a time when the third stimulation/surgical pattern has been completed.

FIG. 5F is a diagram of an operation site at which a surgery-inhibiting nerve-stimulation system is employed, when the operation has been completed.

DETAILED DESCRIPTION OF THE INVENTION

Figure 1E:
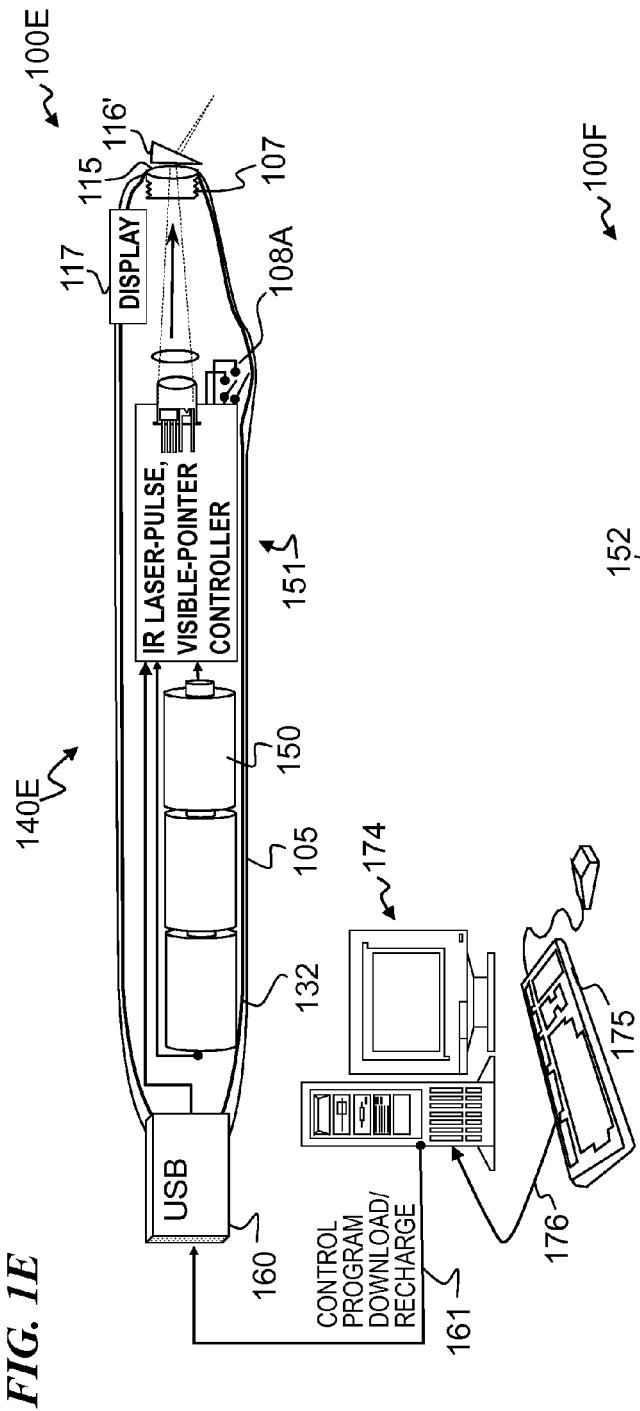
FIG. 1E is a block diagram of a battery-operated nerve-stimulation laser handpiece system 100E.

Although the following detailed description contains many specifics for the purpose of illustration, a person of ordinary skill in the art will appreciate that many variations and alterations to the following details are within the scope of the invention. Very narrow and specific examples are used to illustrate particular embodiments; however the invention described in the claims is not intended to be limited to only these examples, but rather includes the full scope of the attached claims. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component that appears in multiple Figures. Signals and connections may be referred to by the same reference number or label, and the actual meaning will be clear from its use in the context of the description.

CNAP is an abbreviation for compound nerve action potential. CMAP is an abbreviation for compound muscle action potential. As used herein "target neural tissue" is defined as any neural tissue including, but not limited to, peripheral nerves, spinal-cord tissue, and brain tissue of animals, including mammals, and specifically including humans. As used herein "electrical impulse" is defined an electrical current applied to the nerve to initiate an action potential in the neuron. As used herein "stimulation effect" is defined as propagation of an electrical signal within or along neural or muscular tissue. As used herein "single nerve fiber" is defined as a portion of a neuron, namely the axon, which carries action potentials from the cell body to the axon terminal at a synapse, or one or more of the dendrites, which accumulate signals from one or more sources and carry these to the cell body. Many nerve fibers compose a peripheral nerve, such as the sciatic nerve of a leopard frog (*Rana Pepiens*) or a mammal.

For ease of explanation and conciseness, the present invention is described as embodiments of an apparatus and method for optically stimulating nerves and/or generating nerve action potentials. CNAP is one form of nerve action potential. In other embodiments of the invention, substantially similar apparatus and methods are used for optical stimulation of other tissues, such as muscles and/or generating muscle action potentials. CMAP is one form of muscle action potential.

As used herein "hand operated" means operated by some portion of a user's hand or hands, including by one or more of the fingers, thumb, wrist and palm of the hand, or of both hands. In some embodiments, a light-delivery handpiece is hand operated to the extent that the location (i.e., on the nerve or neural tissue) to which light is delivered is determined by positioning the handpiece by hand. In some embodiments, a light-delivery handpiece is also hand operated in that a control device (such as a button, wheel, trigger, iris, shutter, and the like) is operated by hand to control the type of stimulation light (e.g., pulses, intensity, wavelength, pulse train, and the like) and/or timing of the stimulation light.

As used herein "one micron" (a unit generally used when referring to wavelength) is defined as 1.0 micrometer (a unit generally used for circle diameter and other such measurements). As used herein "a spot size of d1 micrometers to d2 micrometers," where d1 and d2 are numbers, is synonymous with "an area of a circle or other shape with a diameter in a range of from d1 micrometers to d2 micrometers," as is known to people skilled in the art. For example, a spot size in a range of 200 micrometers to 600 micrometers is synonymous with an area (e.g., of a circle) with a diameter in a range of from 200 micrometers to 600 micrometers, corresponding to an area with a size in a range of about 31,416 square micrometers to about 282,743 square micrometers, using the formula of Area=$\frac{1}{4}\pi D^2$. In some embodiments, a spot is generated by passing the light that exits an end of an optical fiber through a lens, holographic imaging pattern, or other imaging apparatus.

In other embodiments, spots with diameters of 1 micrometer or smaller, and up to 1000 micrometers (which equal one mm) or larger are used; for example, about 5 micrometers, about 10 micrometers, about 15 micrometers, about 20 micrometers, about 25 micrometers, about 30 micrometers, about 35 micrometers, about 40 micrometers, about 45 micrometers, about 50 micrometers, about 55 micrometers, about 60 micrometers, about 65 micrometers, about 70 micrometers, about 75 micrometers, about 80 micrometers, about 85 micrometers, about 90 micrometers, about 95 micrometers, about 100 micrometers, about 110 micrometers, about 120 micrometers, about 130 micrometers, about 140 micrometers, about 150 micrometers, about 160 micrometers, about 170 micrometers, about 180 micrometers, about 190 micrometers, about 200 micrometers, about 210 micrometers, about 220 micrometers, about 230 micrometers, about 240 micrometers, about 250 micrometers, about 260 micrometers, about 270 micrometers, about 280 micrometers, about 290 micrometers, about 300 micrometers, about 310 micrometers, about 320 micrometers, about 330 micrometers, about 340 micrometers, about 350 micrometers, about 360 micrometers, about 370 micrometers, about 380 micrometers, about 390 micrometers, about 400 micrometers, about 410 micrometers, about 420 micrometers, about 430 micrometers, about 440 micrometers, about 450 micrometers, about 460 micrometers, about 470 micrometers, about 480 micrometers, about 490 micrometers, about 500 micrometers, about 510 micrometers, about 520 micrometers, about 530 micrometers, about 540 micrometers, about 550 micrometers, about 560 micrometers, about 570 micrometers, about 580 micrometers, about 590 micrometers, about 600 micrometers, about 610 micrometers, about 620 micrometers, about 630 micrometers, about 640 micrometers, about 650 micrometers, about 660 micrometers, about 670 micrometers, about 680 micrometers, about 690 micrometers, about 700 micrometers, about 750 micrometers, about 800 micrometers, about 850 micrometers, about 900 micrometers, about 950 micrometers, about 1000 micrometers, about 1.1 millimeters, about 1.2 millimeters, about 1.3 millimeters, about 1.4 millimeters, about 1.5 millimeters, about 1.6 millimeters, about 1.7 millimeters, about 1.8 millimeters, about 1.9 millimeters, about 2 millimeters, about 3 millimeters, about 4 millimeters, about 5 millimeters, or more than about 5 millimeters, or, in other embodiments, in ranges between any two of the above values.

In some embodiments, a laser diode emitting light with a 1.87-micron wavelength stimulates nerves. This wavelength is important because devices capable of generating this wavelength are more available than longer mid-IR wavelengths. In some embodiments, laser-diode light of a 2.1-micron wavelength is used for nerve stimulation. Laser diodes that emit 2.1-micron-wavelength light are currently in research and would most likely work as well as other wavelengths, since this wavelength, when generated by a lamp-pumped solid-state laser, has been shown to be effective in stimulating nerves. In some embodiments, a laser-diode device (having one or more emitters) outputs light that is used for nerve stimulation, wherein the light has a wavelength of between about 1.5 microns and about 6 microns; in various embodiments, for example, the wavelength is in the far infrared at about 1.5 microns, or about 1.51 microns, about 1.52 microns, about 1.53 microns, about 1.54 microns, about 1.55 microns, about 1.56 microns, about 1.57 microns, about 1.58 microns, about 1.59 microns, about 1.6 microns, about 1.61 microns, about 1.62 microns, about 1.63 microns, about 1.64 microns, about 1.65 microns, about 1.66 microns, about 1.67 microns, about 1.68 microns, about 1.69 microns, about 1.7 microns, about 1.71 microns, about 1.72 microns, about 1.73 microns, about 1.74 microns, about 1.75 microns, about 1.76 microns, about 1.77 microns, about 1.78 microns, about 1.79 microns, about 1.8 microns, about 1.81 microns, about 1.82 microns, about 1.83 microns, about 1.84 microns, about 1.85 microns, about 1.86 microns, about 1.87 microns, about 1.88 microns, about 1.89 microns, about 1.9 microns, about 1.91 microns, about 1.92 microns, about 1.93 microns, about 1.94 microns, about 1.95 microns, about 1.96 microns, about 1.97 microns, about 1.98 microns, about 1.99 microns, about 2.0 microns, about 2.01 microns, about 2.02 microns, about 2.03 microns, about 2.04 microns, about 2.05 microns, about 2.06 microns, about 2.07 microns, about 2.08 microns, about 2.09 microns, about 2.1 microns, about 2.11 microns, about 2.12 microns, about 2.13 microns, about 2.14 microns, about 2.15 microns, about 2.16 microns, about 2.17 microns, about 2.18 microns, about 2.19 microns, about 2.2 microns, about 2.21 microns, about 2.22 microns, about 2.23 microns, about 2.24 microns, about 2.25 microns, about 2.26 microns, about 2.27 microns, about 2.28 microns, about 2.29 microns, about 2.3 microns, about 2.31 microns, about 2.32 microns, about 2.33 microns, about 2.34 microns, about 2.35 microns, about 2.36 microns, about 2.37 microns, about 2.38 microns, about 2.39 microns, about 2.4 microns, about 2.5 microns, about 2.6 microns, about 2.7 microns, about 2.8 microns, about 2.9 microns, about 3 microns, about 3.1 microns, about 3.2 microns, about 3.3 microns, about 3.4 microns, about 3.5 microns, about 3.6 microns, about 3.7 microns, about 3.8 microns, about 3.9 microns, about 4 microns, about 4.1 microns, about 4.2 microns, about 4.3 microns, about 4.4 microns, about 4.5 microns, about 4.6 microns, about 4.7 microns, about 4.8 microns, about 4.9 microns, about 5 microns, about 5.1 microns, about 5.2 microns, about 5.3 microns, about 5.4 microns, about 5.5 microns, about 5.6 microns, about 5.7 microns, about 5.8 microns, about 5.9 microns, or about 6.0 microns, or, in other embodiments, in ranges between any two of the above values. In other embodiments, an LED having output wavelengths centered in one of these ranges is used as a source of light to stimulate nerves.

In still other embodiments, one or more laser diodes or LEDs that output shorter wavelengths (including short IR, visible, and/or ultraviolet light) is used as a source of light to stimulate nerves. In particular, visible wavelengths are important because devices capable of generating a great number of different ones of these shorter wavelengths are becoming more available, and use of visible light makes the location of the stimulation signal readily apparent to the user without the use of separate lasers or LEDs as visible markers. On the other hand, longer IR laser wavelengths tend to be more eye-safe (since the liquids and structures in the front of the eye absorb or block longer IR wavelengths), while shorter laser wavelengths can present an eye hazard with respect to which, precautionary protective measures must be taken. Further, different wavelengths have different penetration depths into various tissues, so a selected penetration depth can be achieved by changing wavelength without changing optical power, or by a combination of a selected wavelength and a selected power. In some embodiments, a laser diode having an output wavelength of about 0.95 microns (in the infrared) is used for nerve stimulation. In some embodiments, a laser-diode device (having one or more emitters) outputs light that is used for nerve stimulation, wherein the light has a wavelength of between about 1.5 microns and about 0.2 microns. In various embodiments, for example, the wavelength is in the infrared spectrum at about 0.7 microns, about 0.71 microns, about 0.72 microns, about 0.73 microns, about 0.74 microns, about 0.75 microns, about 0.76 microns, about 0.77 microns, about 0.78 microns, about 0.79 microns, about 0.8 microns, about 0.81 microns, about 0.82 microns, about 0.83 microns, about 0.84 microns, about 0.85 microns, about 0.86 microns, about 0.87 microns, about 0.88 microns, about 0.89 microns, about 0.9 microns, about 0.91 microns, about 0.92 microns, about 0.93 microns, about 0.94 microns, about 0.95 microns, about 0.96 microns, about 0.97 microns, about 0.98 microns, about 0.99 microns, about 1.0 microns, or about 1.01 microns, about 1.02 microns, about 1.03 microns, about 1.04 microns, about 1.05 microns, about 1.06 microns, about 1.07 microns, about 1.08 microns, about 1.09 microns, about 1.1 microns, about 1.11 microns, about 1.12 microns, about 1.13 microns, about 1.14 microns, about 1.15 microns, about 1.16 microns, about 1.17 microns, about 1.18 microns, about 1.19 microns, about 1.2 microns, about 1.21 microns, about 1.22 microns, about 1.23 microns, about 1.24 microns, about 1.25 microns, about 1.26 microns, about 1.27 microns, about 1.28 microns, about 1.29 microns, about 1.3 microns, about 1.31 microns, about 1.32 microns, about 1.33 microns, about 1.34 microns, about 1.35 microns, about 1.36 microns, about 1.37 microns, about 1.38 microns, about 1.39 microns, about 1.4 microns, about 1.41 microns, about 1.42 microns, about 1.43 microns, about 1.44 microns, about 1.45 microns, about 1.46 microns, about 1.47 microns, about 1.48 microns, about 1.49 microns, or about 1.5 microns, or, in other embodiments, in ranges between any two of the above values.

In various other embodiments, for example, the wavelength is in the visible spectrum at about 0.4 microns, or about 0.41 microns, about 0.42 microns, about 0.43 microns, about 0.44 microns, about 0.45 microns, about 0.46 microns, about 0.47 microns, about 0.48 microns, about 0.49 microns, about 0.5 microns, about 0.51 microns, about 0.52 microns, about 0.53 microns, about 0.54 microns, about 0.55 microns, about 0.56 microns, about 0.57 microns, about 0.58 microns, about 0.59 microns, about 0.6 microns, about 0.61 microns, about 0.62 microns, about 0.63 microns, about 0.64 microns, about 0.65 microns, about 0.66 microns, about 0.67 microns, about 0.68 microns, about 0.69 microns, or about 0.7 microns, or, in other embodiments, in ranges between any two of the above values.

In various other embodiments, for example, the wavelength is in the ultraviolet spectrum at about 0.1 microns, or about 0.11 microns, about 0.12 microns, about 0.13 microns, about 0.14 microns, about 0.15 microns, about 0.16 microns, about 0.17 microns, about 0.18 microns, about 0.19 microns, about 0.2 microns, about 0.21 microns, about 0.22 microns, about 0.23 microns, about 0.24 microns, about 0.25 microns, about 0.26 microns, about 0.27 microns, about 0.28 microns, about 0.29 microns, about 0.3 microns, about 0.31 microns, about 0.32 microns, about 0.33 microns, about 0.34 microns, about 0.35 microns, about 0.36 microns, about 0.37 microns, about 0.38 microns, about 0.39 microns, or about 0.4 microns, or, in other embodiments, in ranges between any two of the above values.

In some embodiments, the invention uses a nerve-stimulation signal composed of one or more wavelengths within a range between two numbers selected from the set that includes all of the above listed far-infrared-, visible-, infrared-, or ultraviolet-spectrum wavelengths.

In some embodiments, two or more different wavelengths are used in combination for nerve stimulation. In some embodiments, the different wavelengths have different penetration depths into a given tissue, so in some embodiments, the present invention applies light at a first wavelength from a first laser to achieve a first tissue-penetration depth, but applies light at a second wavelength from a second laser to achieve a second tissue-penetration depth. In some embodiments, a variable amount of each of the two or more different wavelengths is applied simultaneously to achieve a tissue-penetration depth that is variable based on the amounts (intensities) of the first and second light wavelengths. In some embodiments, the two or more different wavelengths are used in combination in cases where the simultaneous combination of two or more different wavelengths achieves higher stimulation results when applied to a specific type of neural tissue than is achieved by the application of either wavelength alone. In some embodiments, the two or more different wavelengths are passed through a single optical fiber for delivery to the target neural tissue.

In other embodiments, different IR wavelengths have different depths of penetration into living tissue (e.g., nerve tissue), and thus one IR nerve-stimulation wavelength is used for penetration to a first depth, and a second IR nerve-stimulation wavelength is used for penetration to a second depth that is different than the first depth. In some embodiments, the two or more different wavelengths are passed through a single optical fiber for delivery to the target neural tissue.

In still other embodiments, different IR wavelengths have different absorption ratios or different stimulation results for different tissue types (e.g., for different types of nerves or neural tissue), and thus one IR nerve-stimulation wavelength is used for stimulation of a first type of neural tissue, and a second IR nerve-stimulation wavelength is used for stimulation of a second type of neural tissue that is different than the first type. In some embodiments, the two or more different wavelengths are passed through a single optical fiber for delivery to the target-neural-tissue area.

In some embodiments, the two or more different wavelengths are generated by two or more solid-state light-emitting devices, such as laser diodes, light-emitting diodes, optically pumped fibers, and the like, and are then combined into a single optical fiber. In other embodiments, the two or more wavelengths are sent through separate parallel fibers or through different cores in a single fiber.

In some embodiments, the optical stimulation light is directed to a very small area of neural tissue, for example in order to stimulate a subset of one or more nerves within a nerve bundle (for example, to stimulate a motor nerve (a nerve that conducts signals from the brain to one muscle or a portion of a muscle), or to stimulate a sensory nerve (a nerve that conducts signals to the brain from a small area of touch-sensing nerves), or an auditory nerve for a single audio frequency, or an optical nerve for a small portion of the visual field or color-sensing spectrum). In some embodiments, such a precision-directed optical signal includes a single optical wavelength; while in other embodiments two or more different IR-stimulation wavelengths are used for stimulating a single nerve or neural tissue area. In some embodiments, two or more different wavelengths provide a stronger stimulation to one nerve cell or one portion of tissue, while in other embodiments two or more different IR-stimulation wavelengths provide different depths of penetration, such that a selected depth or range of depths can be chosen by selecting the wavelength(s) that reach to those depths.

In some embodiments, the optical stimulation light is directed to a larger area of neural tissue, for example in order to stimulate a larger number of nerves or brain cells. It has been found that in some embodiments, the optical stimulation of a single brain cell or a small number of brain cells is ineffective in initiating a neural response, while the optical stimulation of a larger number of brain cells is effective. In some embodiments, delivery of this larger-area optical signal includes a single optical wavelength, while, in other embodiments, two or more different wavelengths are used. In some embodiments, an optical lens, holographic imager, or other imaging device is used to direct light from an optical source (such as a battery-operated laser and/or LED) to the larger area that is to be stimulated. In some embodiments, a grating (e.g., a distributed Bragg reflector having a characteristic grating spacing chosen to eject light from the fiber along the grating length) is imposed along a length (e.g., in various embodiments, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or longer than 20 mm) of the delivery end of a fiber in order that the stimulation optical signal is forced to leave the fiber over a length of the grating, in order that the optical signal is directed to neural tissue over that length of grating on the fiber. For discussion purposes, the dimension along the fiber at its emissive end is called the X-direction. In some embodiments, a plurality of optical fibers is disposed such that their ends emit light across a line perpendicular to their length. For discussion purposes, the dimension perpendicular to the fibers at their emissive end is called the Y-direction. In some embodiments, a plurality of fibers, each having a grating on its end, are placed side-by-side such that light is emitted to a larger area, wherein light has an extent in the Y-direction due to the side-by-side spacings of the multiple fibers and an extent in the X-direction due to the lengths of the gratings on each fiber. In some embodiments, one or more IR stimulation wavelengths are also chosen to be emitted across different extents along a Z-direction, such that a volume of neural tissue having selected extents in the X-direction, Y-direction, and Z-direction is stimulated using the optical stimulation signal.

In some embodiments, a plurality of optical fibers at the delivery tip of the handheld device of the present invention is used to deliver optical-stimulation pulses to different points along the same nerve fiber or bundle at different times. For example, in some embodiments, a first fiber A delivers an optical-stimulation pulse to point $X_A$ along a nerve at a time $t_0$, then later a second fiber B delivers an optical-stimulation pulse to point $X_B$ further along the nerve at a later time $t_4$. In some embodiments, the relative timings of the times of the optical-stimulation pulses at $t_0$ and $t_4$ are selected such that the action potential traveling along the nerve is reinforced or strengthened.

In some embodiments, one nerve is stimulated using different wavelengths applied to different locations along the nerve; for example 1.8-micron-wavelength light can be applied to a first point and 2.2-micron-wavelength light can be applied to a second point. In some embodiments, both the wavelength and the timing of the light stimulation are varied along the nerve.

In some embodiments, a diode laser is employed for nerve stimulation. This is important because a single-diode laser is a very low-cost source compared to free-electron lasers (FEL), fiber lasers or pumped solid-state lasers and the like. A single emitter is used in some embodiments, but, in other embodiments, may not provide enough power for certain purposes. In other embodiments, a multiple-emitter laser-diode device is used, wherein light from a plurality of emitters is directed to a single nerve. In some embodiments, a combiner is used to combine light from a plurality of emitters into a single fiber. In some embodiments, one or more side-emitting lasers are employed, while in other embodiments surface-emitting lasers are used. In some embodiments, a combination of different laser types is used, e.g., based on the need to generate certain combinations of wavelengths or powers.

In some embodiments, the laser-diode device is coupled to one or more optical fibers that convey the light to the location at the nerve for stimulation. In other embodiments, the laser diode itself is positioned at the point of stimulation, eliminating the need for the optical fiber.

In some embodiments, a WDM (wavelength-division multiplexing) coupler is used to combine two or more wavelengths to be transmitted through a fiber to be ultimately delivered to nerve tissues. Such couplers combine light at differing wavelengths supplied to two or more optical-fiber ports, to produce a single multi-wavelength beam at an additional optical-fiber port. WDM couplers are well known in the field of telecommunication systems; an early example is described in U.S. Pat. No. 4,296,995, with a more recent example described in U.S. Pat. No. 5,796,889. In some instances of each of the embodiments described herein, a WDM coupler is used to couple light from the emitters (e.g., laser diodes or LEDs) into an optical-fiber structure.

In at least one embodiment, it is important to make the fiber core's size or sizes small for stimulating smaller nerves. More to the point, given the small size of some nerve fibers, a fiber core and a laser diameter corresponding to (e.g., equal to or smaller than) the diameter of this nerve fiber need to be provided. In some embodiments, a fiber core much smaller than the nerve fiber is used. For example, in some embodiments, a fiber core having a one-micron (or smaller) diameter is used. In other embodiments, fibers having core diameters of 100 micrometers or larger are used. In some embodiments, the optical fibers are made of a glass such as silica or other suitable material (such as plastic). In some embodiments, the optical-fiber bundle used for imaging the tissue being stimulated and observed is made of plastic and/or glass fibers. In some embodiments, multiple small-core fibers can be used to simulate multiple small nerves simultaneously or independently.

In at least one embodiment, a fiber-coupling technique is implemented to increase the brightness of light delivered from the battery-operated handpiece by coupling light from a plurality of laser emitters (e.g., from a laser-diode bar) for biological stimulation (i.e., nerve or tissue stimulation). Many different coupling techniques may be employed to increase the brightness of a laser-diode bar. For example, co- and contra-directional and evanescent coupling are some of the coupling techniques known in the art.

In some embodiments, a single-emitter laser diode (such as an 1850-nm wavelength single emitter available from Princeton Lightwave company, for example laser diode described at www.princetonlightwave.com/content/HP%20Single%20Element%20Laser%20version%202.pdf or other suitable diode is implemented and used to generate laser light of some efficacious wavelength to a particular target nerve or tissue. As described elsewhere herein, such single-emitter laser diodes may be side-emitting and/or surface-emitting laser diodes.

In some embodiments, there is a combining and co-alignment of a visible wavelength with the IR-stimulation light in order to provide a visual cue for directing the IR-stimulation light used for stimulating a nerve or other tissue. Laser light in the IR range (e.g., 700 nm-1850 nm or longer) is not visible to the human eye. Due to this fact, as a practical matter, this IR optical-stimulation light cannot be easily aimed to a particular target (e.g., a nerve fiber) using the naked eye. In some embodiments, visible light (i.e., light in the 400 to 700 nm range from a laser diode, L.E.D., or other source) is also inserted into the optical fiber or fiber bundle and used to guide movement of the emitting end of the fiber to aim the IR light so as to allow the IR light to be applied in an efficacious manner to, for example, stimulate a nerve fiber. In some embodiments, the visible light is passed through one or more fibers or fiber bundles (i.e., this can be using the same fiber(s) as the IR optical-stimulation light, or in other embodiments, using a separate fiber) so as to provide a target spot.

Next (or simultaneously), IR light is passed through the same one or more fibers to the same point on a nerve fiber that the visible light previously illuminated or currently illuminates. In some embodiments, both the IR light and visible light have separate light sources that are coupled into a commonly shared optical-fiber structure, whereas, in other embodiments, a separate optical-fiber structure is used to channel each wavelength of light. In some embodiments, an optical-fiber structure is used in which at least some fibers are used to transmit light of one wavelength, while at least some other fibers are used to transmit light of a different wavelength (for example, in some embodiments, different fibers are used to carry the visible light, the IR-stimulation light, and/or the cutting/ablating/cauterizing light, and/or to return the imaging light obtained from the tissue being targeted). In some embodiments, still other optical fibers are used to carry control-light signals to and from the handpiece, such that an operator holding the handpiece can selectively command a remote light source to do his/her bidding. As described below, in some embodiments, these optical-fiber structures are operatively coupled to a glass, ceramic plastic or some other type of ferrule or plug made from a non-magnetic material.

In some embodiments, the visible laser light is selected from one or more wavelengths empirically selected to selectively show a visible difference in reflected brightness when directed at nerve fibers as compared to blood vessels, muscles, connective and other tissues. For example, in some embodiments, a combination of red, green and/or blue laser or LED light is used. In some embodiments, green light has been found to be more effective (as an indicator of where the fiber delivery head is pointing) than red or blue light alone. In some embodiments, a fiber bundle (with plastic and/or glass fibers) capable of obtaining image information and transmitting optical two-dimensional color imaging to a remote location is used to convey image information from the subject (e.g., someone in an MRI machine) to a remote viewing location. In some embodiments, a machine-vision system is used to distinguish color features of tissues (e.g., hue, tint, and/or brightness) and/or shapes of tissues from a digital or video image, and to display an enhanced image (e.g., one using enhanced or false-color image information) derived from the image.

In some embodiments, an IR video imager is used to obtain and display the location of the IR-stimulation signal without the addition of visible-wavelength light. In some embodiments, a fiber bundle or other structure capable of obtaining and transmitting optical two-dimensional IR imaging to a remote location is used to convey image information to a remote IR imager.

In some embodiments, a second, high-power laser signal (called the "surgical signal") is generated in (e.g., by a supplemental laser diode, or by applying more electrical power to the stimulation laser diode), or coupled through, the handpiece to the stimulation area, wherein the operator can stimulate nerve tissue using a first stimulation-wavelength-and-power optical signal (called the "stimulation signal") to distinguish tissue that is to be saved from tissue that is to be cut or destroyed, and then use the high-power laser light to cut, ablate, or cauterize the tissue to be destroyed. In some such embodiments, the optical-stimulation signal is provided by a first laser source (e.g., a laser diode, optically-pumped fiber laser, or the like), and the optical surgical signal is provided by a second laser source of higher intrinsic power or energy, or of a different wavelength more suited for surgical purposes (e.g., another laser diode, optically-pumped fiber laser, or the like). In other embodiments, a single laser source is used for both the optical stimulation signal and the optical surgical signal, wherein a parameter of the signal is changed to achieve one function or the other (e.g., in some embodiments, the optical surgical signal is obtained by shortening the pulse length, for example by Q-switching, in order that a given amount of energy is delivered in a very short time to ablate a small area of tissue, or by lengthening a pulse length having a constant average energy or by increasing the number of pulses sent in a short time period in order that one or more pulses with a given average power integrate over time to heat the tissue being treated).

In some embodiments, the targeting of various nerve fibers is performed manually (e.g., by manually moving a handpiece to locate the delivery end of an optical fiber so that light energy may be directed on to the nerve to be stimulated).

In some embodiments, as is disclosed below, the pulse shapes of the light generated by or controlled from the device are controlled through the use of a light-pulse device that regulates the light under control of a computer, microprocessor or CPU (e.g., x86 series, Intel 8051 CMOS series utilizing certain computer-executable instructions stored to a computer-readable medium, or under control of a non-computer, non-programmed electronic circuit).

A computer-readable medium is defined to be a medium for carrying or having computer-executable instructions or data structures stored thereon. Such computer-readable media may be any available medium that is accessible by a general-purpose or special-purpose computer system. By way of example, and not limitation, such computer-readable media can include physical storage media such as RAM, ROM, or EPROM, removable media such as CD-ROM or other optical-disk storage, diskettes, magnetic hard-disk storage or other magnetic-storage devices, or any other media which can be used to carry or store desired program code means in the form of computer-executable instructions, computer-readable instructions, and/or data structures and which may be accessed by a general-purpose or special-purpose computer system; this physical storage media may be fixed to the computer system as in the case of EPROM or a magnetic hard drive, or removable as in the case of an EEPROM on a USB-connected device (e.g., flash memory device) or CDROM, DVD, or diskette, or can include network-connected storage (such as a hard drive connected to the internet.

In some embodiments, various methods, systems, apparatus or the like are employed to guide the IR light to its target nerve fiber. In some embodiments, a disposable, biologically inert, non-metallic and/or non-magnetic optical tip at the end of the handpiece is provided. In some embodiments, this tip is adjustable or interchangeable so as to allow for the spot size to vary depending on type or location of nerve to be stimulated. In some embodiments, this tip is configured on a light pen, pointer or similar handheld device so as to allow the user to manually target a particular nerve fiber or series of fibers. In some embodiments, this optical tip is encased in or affixed to a disposable plastic sheath (e.g., a sterile sheath that is used once for an operation and then discarded), whereas in other embodiments it is encased in an end of the aforementioned light pen, pointer or similar device. In some embodiments, a sterile disposable sheath is applied to the handpiece before each use, and is discarded afterwards. In other embodiments, the handpiece, light pen, pointer or the light-delivery device itself is provided in a sterile condition, and is inexpensive enough to be disposable.

In some embodiments, the optical path is selectively interruptible by a mechanical shutter and/or variable aperture that allows the user to control the passage of laser light (i.e., the visible signal, optical-stimulation signal, optical surgical signal or the like) through the optical tip. In some embodiments, the shutter is used to start and stop the light passing through the optical tip. In some embodiments, as with the other components that form the delivery end of the device, this shutter and/or aperture is made from a non-metallic material such as a plastic, ceramic or similar material. In some embodiments, the variable aperture is adjustable to control the amount of light (e.g., the power and/or size of the spot), which, in some embodiments, also includes the start and stop of the light signal to the target tissue. In some embodiments, an iris diaphragm is provided to regulate the variable aperture through which light passes. In some embodiments, a non-metallic material such as a plastic, ceramic or similar material is used to construct the iris diaphragm. In some embodiments, the optical tip is secured to, or with, a ferrule or similar.

In some embodiments, the flow of stimulation and/or pointer light, be it IR or visible, is controlled via a mechanical linkage incorporated into the above-described handpiece, light pen or pointer. In such an embodiment, the linkage includes a trigger-like device that, when depressed or otherwise manually controlled, controls the flow of the above-described light.

In some embodiments, a sterile, disposable covering or sheath constructed from plastic, polymer or some other substance is placed over the above-described handpiece, light pen or pointer. This disposable covering is then discarded after use of the handpiece, light pen or pointer. In some embodiments, this disposable covering includes one of a plurality of different beam-shaping optics that allow for different beam characteristics for different applications. In some embodiments, IR light in a higher or lower wavelength range may be more or less efficacious. For example, near-IR light (e.g., in the 700-1400 nm wavelength range) may be better for nerve-damage repair (or for cutting, ablating or cauterizing), while short-wavelength IR light (e.g., in the 1400-3000 nm range) may be better for vagus nerve stimulation, etc. The efficacy of a particular IR wavelength can be determined through empirical testing and/or modeling.

In some embodiments, a power controller is implemented that is operable to provide programmable pulse shapes (e.g., pulse width, repetition rate, etc. that can be varied in a programmable manner). In some embodiments, a laser light source is operatively coupled to a timer or pulse-regulating device that controls the shape, magnitude, cycles or other features of a light pulse. In some embodiments, this pulse-regulating device is used in conjunction with the above-described shutter, while in other embodiments it is used alone. In some embodiments, the pulse-regulating device is a remote control that is used from outside of the magnetic field generated by an MRI device, so as to not present a danger to an individual using an MRI device, while the hand-held device generating the stimulation light includes a receiver to obtain control information from the remote control but is made of materials that are compatible with use in the field of the MIR machine.

In some embodiments, a thumb/finger control mechanism includes a non-magnetic (e.g., plastic) component mechanism that is optically assessed in order to control the light source to drive a particular pulse shape (e.g., an optical assessment signal (e.g., an unmodulated laser or LED light signal) is sent to the component mechanism that is part of the thumb/finger control mechanism, and the state of the component mechanism, which is a function of the position of the thumb/finger control mechanism, changes a characteristic of the light and returns it as an optical control signal). Specifically, whereas in some embodiments programmable pulses are automatically generated, in at least one embodiment, pulse shapes can be modified using a thumb/finger control that can modify the pulse width, repetition rate and the like. In some embodiments, a knob, toggle or other switch is used that allows a user to modify the pulse width by turning, for example, a knob to a particular position. The use of a knob, toggle or the like to modify the various pulse shapes can be determined through assessing the ergonomic benefits of a particular switch and switch location on the above-described handpiece or light pen.

In at least one embodiment, a laser-wavelength-selective device is implemented to couple the visible light and provide power control or laser-safety monitoring or output-power measurement. In some embodiments, this is done with a beamsplitter (e.g., a 10%-90%) to couple 10% of the visible laser signal into the optical beam having the stimulation-wavelength signal.

In some embodiments, the visible-light pointer includes a point-to-line or point-to-area beam spreader (e.g., a hologram) that generates a centered pattern (e.g., a cross-hair pattern with perpendicular lines that intersect where the stimulation will occur) that shows where the IR nerve-stimulation light will be (or is) directed, while providing better usability for the surgeon or technician by allowing the user to align one of the lines with the nerve.

In the discussions of the present invention, for brevity many embodiments describe laser diodes that are battery-powered. In any of the embodiments of the present invention, the battery can be replaced by another suitable self-contained energy-storage device (e.g., battery-like devices or other power source, such as capacitors, chemical energy, rotational flywheel energy, spring energy and the like that power the laser directly (e.g., chemical lasers) or are used to generate electricity (e.g., flywheel or spring-driven electrical generators); and/or a self-contained power receiver such as a coil for receiving AC magnetic or RF energy, a photovoltaic cell for receiving optical energy, and the like). Many embodiments, for brevity, describe laser diodes as the sources of optical radiation (IR or visible) however other embodiments use LEDs or diode-pumped rare-earth-doped optical fiber sources of laser, super-luminescent, or other radiant energy for the stimulation optical beam, the pointer visible beam, or both. Further, the exemplary embodiments shown include some features in some embodiments and not in others. It is to be understood that other embodiments of the present invention use combinations of features selected from the various figures and descriptions to achieve identical or similar operations.

FIG. 1A is a block diagram of a battery-operated nerve-stimulation laser handpiece system 100A. In some embodiments, system 100A uses a battery-operated nerve-stimulation handpiece 140A. In some embodiments, laser-diode assembly 111 is operatively coupled to a tip 107 that contains one or more light-transmitting optics or lenses 115. Some embodiments further include one or more lenses 114 for beam focusing, collimating, and/or shaping. In some embodiments, control of this IR and/or visible light is via trigger 108A (which, in some embodiments, includes one or more internal separately activateable switches) being pressed or otherwise activated by user 89—typically by the finger or thumb of user 89. In some embodiments, trigger 108A includes a flexible membrane portion of housing 132 that covers an internal switch that is operatively coupled to a laser controller/power controller 152 (alternatively designated light-emitting-source controller 152) that together with laser/light-emitting-source assembly 111 form light source 151. In some embodiments, power source 150 (also called self-contained energy source 150, which includes, e.g., batteries, in some embodiments) is interruptably connected to light source 151 via on-off switch 112A. In some embodiments, tip 107, on-off switch 112A and handpiece housing or handle 132 are grouped together and protected via a disposable replaceable sheath 105 to form handpiece 140A. In some embodiments, tip 107 forms a part of handpiece housing 132, and these are together inserted into the disposable sheath 105 via an opening 113, which is then folded over and sealed (e.g., via pressure-sensitive adhesive). In other embodiments, tip 107 and its lens 115 form a part of the disposable sheath 105 (this allows the optics to be interchanged with other disposable sheaths 105 having different optics by swapping sheaths, in order to easily obtain the desired optical pattern uniquely suited for nerve, brain or other tissue stimulation and avoiding possible contamination from the lens if the lens were left in place). Such a sheath 105 is pulled over the length of handpiece housing 132 until the light-transmitting optics or lens 115 of the tip 107 is flush or engaged with the opening 124 of housing 132. In some embodiments, the pieces of handpiece 140A are all manufactured from substantially non-metallic, non-magnetic materials such as plastics, polymers, ceramics or the like. In some embodiments, the light pattern desired from the optics is empirically determined by testing various patterns on various tissues and observing the reaction obtained. In other embodiments, the sheath 105 provides a clear window that covers tip 107 and its lens 115. In some embodiments, tip 107 and its lens 115 are configured to be an interchangeable optics mechanism (e.g., a threaded or snap-in imaging adaptor configured to be easily swapped), several different ones of which are provided as a kit with handpiece 140A.

FIG. 1B is a block diagram of a battery-operated nerve-stimulation laser handpiece system 100B. In some embodiments, reference numbers of elements shown in FIG. 1B refer to like-numbered elements described above for FIG. 1A. In some embodiments, handpiece 140B has few if any switches (such as 112A and 108A described for FIG. 1A), but rather is activated wirelessly by remote-control device 141. This helps prevent movement of the handpiece when the light is activated (in contrast to the embodiment shown in FIG. 1A, which might move when the user's finger presses on switch 108A). Instead, remote controller 141 includes one or more switches 108B (e.g., activated by user 89's foot, or opposite hand, or otherwise (such as a microphone and voice-recognition software on a computer, activated by the user's voice commands)), a controller 104B that interprets the activation of the one or more switches 108B and sends commands through wireless transmitter 109B to wireless receiver/controller 112B, which then activates the light-emitting functions of light source 151. Other aspects of system 100B are similar to those described for FIG. 1A.

FIG. 1C is a block diagram of a battery-operated nerve-stimulation laser handpiece system 100C. In some embodiments, system 100C uses a battery-operated nerve-stimulation handpiece 140C. In some embodiments, emission of IR and/or visible light from light source 151 is controlled via a foot-trigger 108C being pressed by the foot of user 89, which is operatively coupled to switch 112C via mechanical linkage 106C that is within cable sheath 109 (e.g., a flexible plastic rod in a flexible plastic tube). In some embodiments, handpiece 140C from tip 107 to cable sheath 109 are together inserted into disposable sheath 105 though opening 113, which is then closed and sealed to cable sheath 109 (e.g., with a twist-tie or pressure-sensitive adhesive). In some embodiments, other options for sheath 105 are as described for FIG. 1A. Other aspects of system 100C are similar to those described for FIG. 1A.

FIG. 1D is a block diagram of a combined light source or laser assembly 111. In some embodiments, light source 111 includes an IR-laser-diode emitter 101 that emits a wavelength of light useful for tissue stimulation and a front lens 104. Some embodiments further include a visible laser or LED 102 and a beam-combiner optic or optics 103 (for example, a highly reflective minor 119 and a beam combiner plate 118, such as a dichroic minor that is highly reflective of one wavelength (e.g., the visible-light wavelength of emitter 102) and highly transmissive of another wavelength (e.g., the stimulation-light wavelength of emitter 101). Some embodiments further include a therapeutic (e.g., surgical) beam generated by a high-power laser 147 and combined using a beam-combiner optic or optics 116 (similar to beam combiner 103, except for the wavelengths for which the dichroic minor is configured). In some embodiments, combining the two or more beams into a single beam makes the downstream optics simpler. In other embodiments such as described below for FIG. 3, light source 111 generates two or more beams (e.g., parallel beams, in some embodiments), wherein the handpiece is configured to deliver the light in the separate beams to the desired location using suitable optics (e.g., some embodiments include two or more visible pointer beams that form separate beams that form separated spots, and the optics is arranged to focus the two visible beams into a single spot only when the invisible (IR) stimulation beam is in focus).

In some embodiments, one or more visible-light sources 102 emit visible indicator light (i.e., light having one or more visible wavelengths suitable for indicating to a user where the stimulation light or therapeutic (e.g., surgical) light will be delivered), which is coupled by light-beam combiner and/or coupler 103 to combine with the optical beam from stimulation-wavelength laser 101. In some embodiments, visible-light sources 102 include one or more visible-light LEDs, incandescent lamps, and/or laser diodes emitting light at one or more different wavelengths (e.g., 0.45-micron blue light (e.g., gallium-indium nitride devices), 0.55-micron green light (e.g., gallium-indium nitride LED or laser-diode devices), 0.63-micron red light (e.g., gallium-arsenide LED or laser-diode devices), or other wavelengths useful for pointing and/or delivering to the user function-state information, such as different colors or pulsing characteristics to indicate which function has been selected) under control of light-emitting-source controller 152.

In some embodiments, one or more high-power laser sources 147 emit high-power laser light (or very-short-pulse laser light), which is coupled by light-beam combiner 116 and/or coupler 103 into the output beam. In some embodiments, high-power laser sources 147 include one or more high-power lasers or laser diodes or optically-pumped-fiber lasers emitting light at one or more different wavelengths (e.g., 1.55 microns, or other wavelengths useful for surgical purposes) under control of light-emitting-source controller 152. In some embodiments, the high-power laser light effects a burning or cutting operation where heat results from the laser interaction with the tissue (i.e., absorbing photon energy from the laser light and converting it to heat). This can result in cauterizing the surrounding tissue and reducing bleeding. In other embodiments, the very-short-pulse laser light (e.g., from one or more femtosecond-pulse lasers that concentrate power into a very short time period, such as are described in U.S. Patent Application Publication US 2004 0243111 A1 by Mark Bendett et al. and U.S. Patent Application Publication US 2004 0243112 A1 by Mark Bendett et al., both of which are incorporated by reference) effects an ablation or tiny explosion that removes tissue with substantially no heating of surrounding or underlying tissue.

FIG. 1E is a block diagram of a battery-operated nerve-stimulation laser handpiece system 100E. In some embodiments, system 100E includes a handpiece 140E having a programming and/or recharging port 160 (such as a USB port) that is removably connectable to a computer system 174 for recharging power system 150 (e.g., its batteries) and/or for programming the controller of light source 151. Such programming includes, in some embodiments, one or more predetermined characteristics of the light output such as the duration (e.g., the number of milliseconds the pulse is active), number (e.g., the number of pulses in one train, or the total number of pulses allowed in any one session), power (e.g., the total number of watts or the watts per area), shape (e.g., rising trapezoid, flat-top, or falling trapezoid or other shape of each pulse), envelope (e.g., the overall shape of the pulse train, for example, rising trapezoid, flat-top, or falling trapezoid or other shape of the envelope of a series of pulses) or like characteristics of the single pulse or pulse train that is initiated by user activation of trigger 108A (which, in some embodiments, includes one or more internal separately activateable switches). In other embodiments, the programming and/or rechargeability functions described here are combined into any of the other handpieces 140 (with any letter suffix) of the present invention described herein. In some embodiments, a computer-readable medium stores programs and/or computer-executed instructions that are loaded into PC 174 and/or into handpiece 140E that control the method performed in handpiece 140E and/or the user interface to handpiece 140E. In some embodiments, computer system 174 includes a user-input device such as keyboard 175 that communicates with the computer-processing unit of computer system 174 through connecting link 176, which may be a hardware-connecting link 176 or a wireless connecting link 176. In some embodiments, a wedge-shaped prism beam combiner 116' is located at the end of delivery tip 107 of handpiece 140E.

Figure 1F:
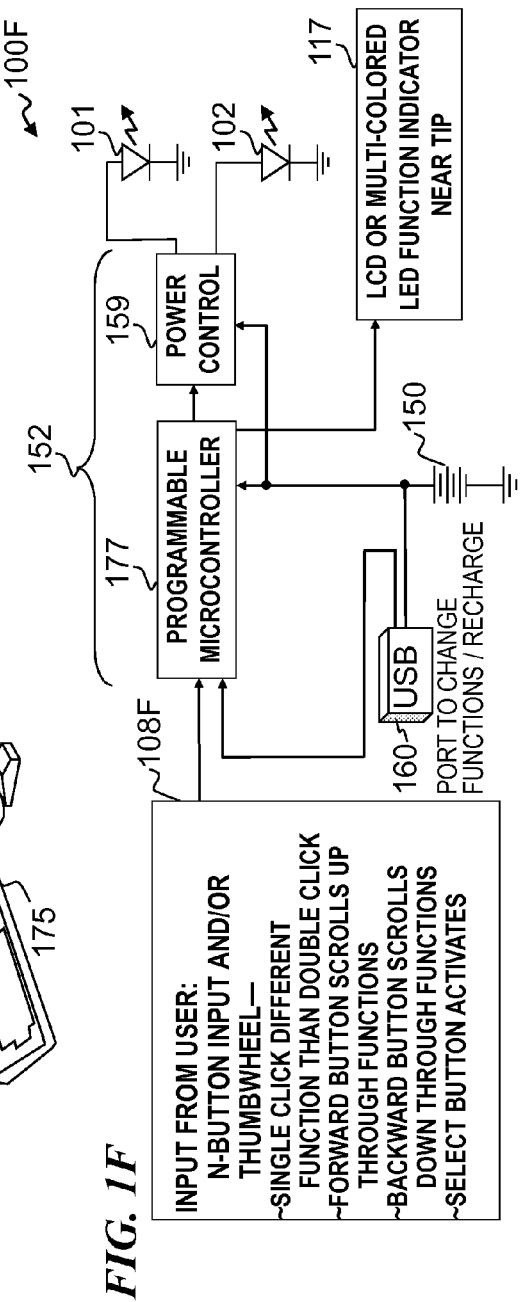
FIG. 1F is a block functional diagram of battery-operated nerve-stimulation laser handpiece system 100E.

FIG. 1F is a block functional diagram of battery-operated nerve-stimulation laser handpiece system 100E as shown in FIG. 1E described above. Box 108F shows various input indications received from a user-manipulating trigger 108A of FIG. 1E described above. For example, in some embodiments, an array of one or more buttons and/or a rotateable thumbwheel are activated by the user to initiate one or more functions (e.g., turning on the pointer laser, the nerve-activation laser, or the therapeutic laser, or changing their function). In some embodiments, a single click on a button will cause one function to be performed, while two clicks in short succession produce a different function. In some embodiments, the USB interface 160 allows the program in programmable controller 177 to be changed, and/or provides a charging mechanism for batteries 150, which are later used to power programmable controller 177 for functionality and power controller 159 that is used to drive the laser and/or LED light source(s) (e.g., 101 and 102). In some embodiments, a display 117 is provided (e.g., and LCD screen or one or more LEDs of one or more colors) that displays text and/or graphics to show the activation state of the lasers, and their characteristics such as power, pulse length, repetition rate and the like.

Figure 1G:
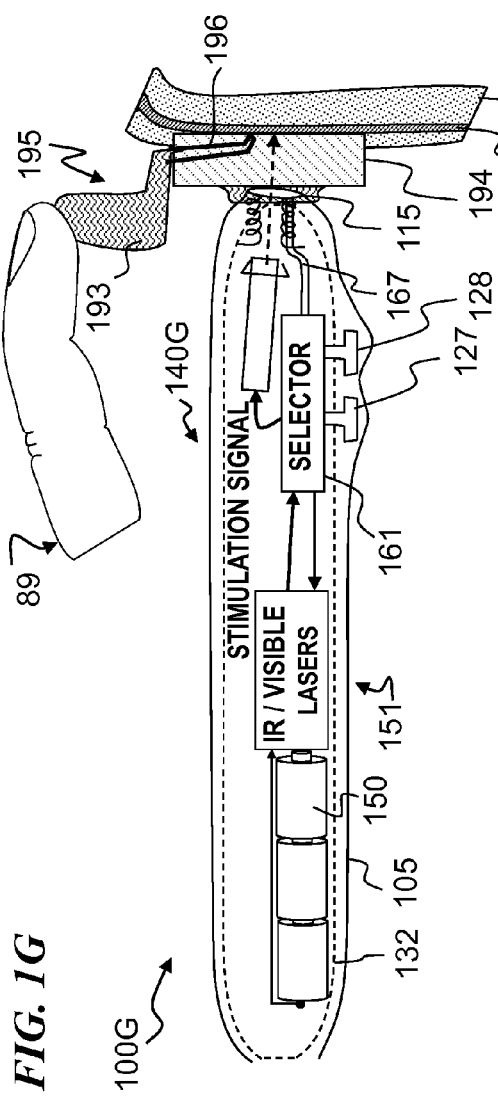
FIG. 1G is a block diagram of battery-operated nerve-stimulation laser handpiece system 100G.

FIG. 1G is a block diagram of battery-operated nerve-stimulation laser handpiece system 100G having a mister 195 and/or focus plate 194. Handpiece 140G is similar to handpiece 140C of FIG. 1C, but with the addition of a spring-loaded-tip light controller 167. In some embodiments, focus plate 194 provides a predetermined optical distance between handpiece 140G and the nerve 69 that is being stimulated. In some embodiments, focus plate 194 includes wetter 195 having a squeeze bulb 193 containing a sterile saline solution and/or index-of-refraction-matching liquid that is applied by squeezing drops through nozzle 196, either directly onto nerve 69 in tissue 68, and/or under (i.e., providing a clean gap-free interface between plate 194 and nerve 69) and/or on top of, focus plate 194 (i.e., providing a clean gap-free interface between plate 194 and handpiece 140G). In some embodiments, lens 115 is mounted on a spring-loaded selector-activation rod 167, such that when the tip of handpiece 140G is pressed onto a nerve or onto focus plate 194, the visible pointer-light source and/or the stimulation-light source is activated and pointer and/or stimulation light is emitted. In some such embodiments, selector buttons 127 and 128 are omitted, such that the handpiece 140G is selectively activated only when tip 167 is pressed against the subject or other object. In other embodiments, one or more of the activation signals to the various light sources is activated by switches 128 and/or 127, and/or by a remote activation switch as described elsewhere herein. In some embodiments, a mechanical shutter replaces selector 161, and is activated (e.g., opened) to allow light to be emitted only when the tip 167 is pressed (in some embodiments, other activation signals are also required, but the light is not emitted until the tip is also pressed). In some embodiments, such a spring-loaded tip helps to ensure that the correct focal distance is obtained before the laser is activated. In some embodiments, focus plate 194 (made of glass, plastic, or other material transparent to the light wavelengths of interest) is of a thickness such that when lens 115 is pressed on one face of focus plate 194 with stimulation light being emitted, and the other face of focus plate 194 is pressed onto nerve 69, the light is focussed to a spot size that is desired. In some embodiments, use of focus plate 194 also keeps the nerve moist and alive by preventing evaporation. In some embodiments, wetter 195 can be used to apply a moistening liquid or gel onto nerve 69 or onto the nerve-side face and/or outside face of focus plate 194 (besides keeping the nerve moist and alive, this provides an index-of-refraction matching, which reduces reflections; drying can cause tissue damage and changes the reflectivity to the stimulation light signal).

Figure 1H:
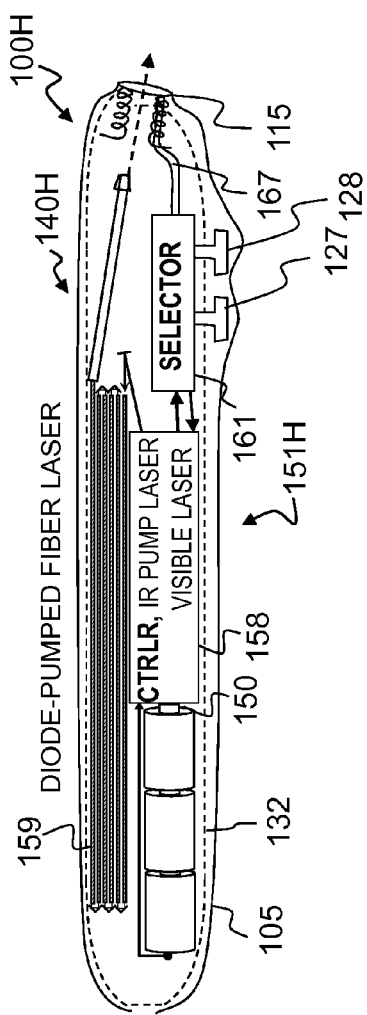
FIG. 1H is a block diagram of battery-operated diode-laser-pumped rare-earth-doped fiber emitter nerve-stimulation handpiece system 100H.
Figure 1I:
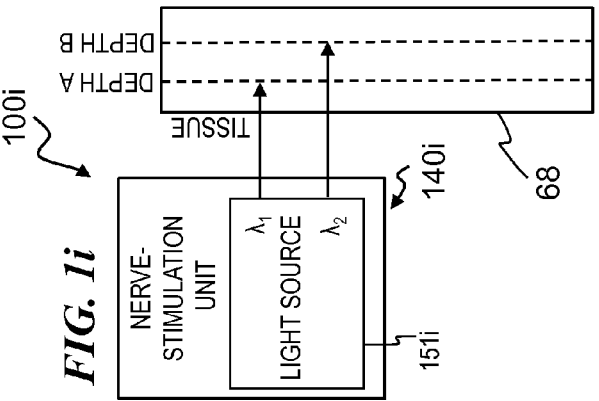
FIG. 1i is a block diagram of a nerve-stimulation system 100i.

FIG. 1H is a block diagram of battery-operated diode-laser-pumped rare-earth-doped fiber emitter nerve-stimulation handpiece system 100H. In some embodiments, the invention uses fibers and pump-diode lasers such as described in U.S. patent application Ser. No. 11/426,302, filed Jun. 23, 2006 and titled "APPARATUS AND METHOD FOR A HIGH-GAIN DOUBLE-CLAD AMPLIFIER," U.S. patent application Ser. No. 11/488,910, filed Jul. 17, 2006 and titled "APPARATUS AND METHOD FOR GENERATING CONTROLLED-LINEWIDTH LASER-SEED-SIGNALS FOR HIGH-POWERED FIBER-LASER AMPLIFIER SYSTEMS," U.S. Provisional Patent Application Ser. No. 60/748,379, filed Dec. 7, 2005 and titled "APPARATUS AND METHOD FOR AN ERBIUM-DOPED FIBER FOR HIGH-PEAK-POWER APPLICATION," and U.S. Provisional Application Ser. No. 60/733,977, filed Nov. 3, 2005 and titled "APPARATUS AND METHOD FOR A WAVEGUIDE WITH AN INDEX PROFILE MANIFESTING A CENTRAL DIP FOR BETTER ENERGY EXTRACTION," each of which is incorporated herein by reference. In some embodiments, a pump laser diode emits pump light at about 960-micron wavelength, the doping species of the fiber is chosen (using a table of such elements that are well known to persons of skill in the art) to obtain a wavelength suitable for nerve or other tissue stimulation. In some embodiments, controller and laser device 158 includes electronics and light emitters. In some embodiments, one or more of the light emitters operate with visible wavelengths for pointer use, and one or more light emitters in wavelengths suitable for pumping the fiber emitters 159 (i.e., the pump lasers emit a wavelength suitable for pumping the fiber laser segment(s) 159). In some embodiments, fiber emitters 159 include feedback devices such as mirrors, gratings or the like, and operate as lasers. In other embodiments, the fibers serve as superluminescent emitters, wherein spontaneous emission of the fibers is amplified in the fibers. Other aspects of system 100H are as described in the above figure descriptions.

FIG. 1$i$ is a block diagram of a nerve-stimulation system 100$i$. In some embodiments, system 100$i$ includes a nerve-stimulation unit 140$i$ of such small size to be readily hand held by a human user, wherein the nerve-stimulation unit 140$i$ includes a light-emitting source 151$i$ that is operative to emit an optical stimulation signal at a first wavelength $\lambda_1$ capable of directly stimulating a nerve of a subject. In some embodiments, light-emitting source 151$i$ is operative to emit an optical stimulation signal at a second wavelength $\lambda_2$ capable of directly stimulating the nerve of the subject. In some embodiments, the second wavelength $\lambda_2$ is different than the first wavelength $\lambda_1$ and has a different penetration depth into tissue 68. In some embodiments, light at the first wavelength $\lambda_1$ is applied to achieve a first tissue-penetration depth A, and light at the second wavelength $\lambda_2$ is applied to achieve a second tissue-penetration depth B.

Figure 2:
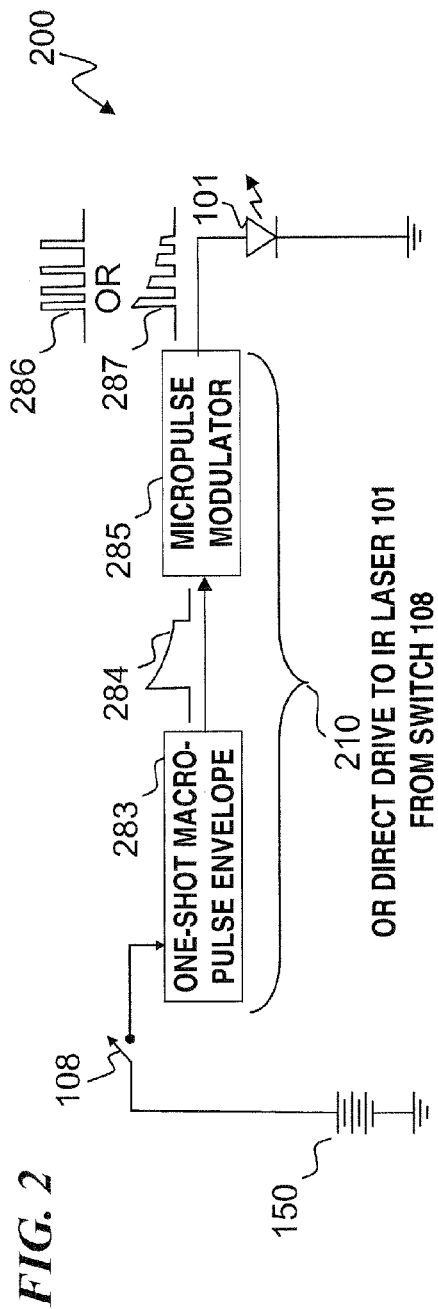
FIG. 2 is a block circuit diagram of battery-operated nerve-stimulation laser handpiece system 200.

FIG. 2 is a block circuit diagram of battery-operated nerve-stimulation laser handpiece system 200. In some embodiments, power source 150 is connected to circuit 210, which provides drive current to stimulation-wavelength laser 101. In some embodiments, circuit 210 includes a one-shot circuit 283 that outputs macro pulse envelope waveform 284 of a suitable shape (flat, rising, or falling or other shape), repetition and duration, which signal is then optionally modulated with micro-pulse modulator 285 to obtain a suitable train of one or more shorter-duration pulses, such as waveform 286 or 287, and laser diode 101 outputs stimulation light having a corresponding amplitude light output (some embodiments switch the order of components, placing the micro-pulse circuit 283 first and use the one-shot 283 as an envelope modulator, other embodiments use other orders of components or substitute circuit functions (e.g., software or microcode control of a power transistor driven by a microcontroller)). In other embodiments, circuit 210 is simply a direct drive of an infrared laser diode 101 from switch 108.

Figure 3:
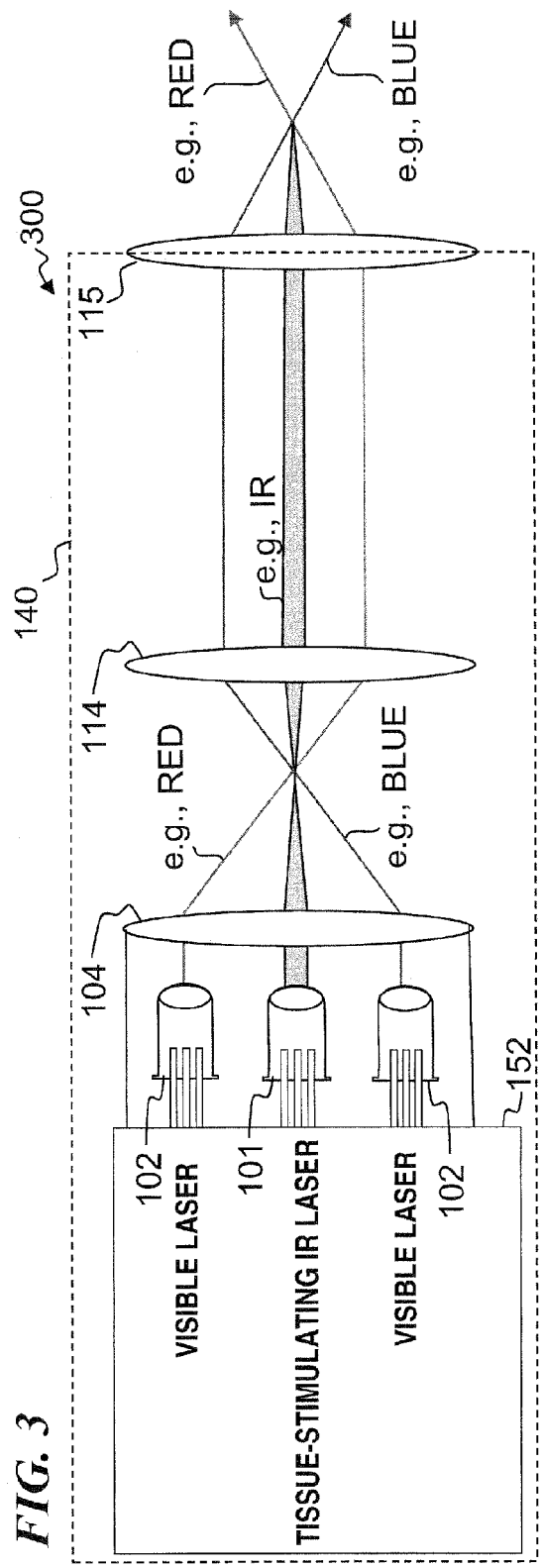
FIG. 3 is a block diagram of focus-indicating nerve-stimulation laser handpiece system 300.

FIG. 3 is a block diagram of focus-indicating nerve-stimulation laser handpiece system 300. In some embodiments, one, two, or more visible laser diodes 102 are arranged around (e.g., in some embodiments, one on either side and parallel with) the beam of the tissue-stimulating laser diode 101. A single lens 115 or a series of two or more lenses (e.g., 104, 114, and 115) are used to collimate and focus the nerve-stimulation beam to a point, or a suitable shape of a desired size. This optical path causes the two pointer beams (e.g., a red pointer beam from the top laser 102 and a blue beam from the bottom laser 102) to cross at the optimal focus depth to obtain the desired focus of the non-visible IR nerve-stimulation beam. If the lens 115 at the tip of the handpiece 140 is too close, the blue-beam's spot will be below the red-beam's spot, or if the lens 115 at the tip of the handpiece 140 is too far from the nerve, the blue-beam's spot will be above the red-beam's spot. When at the correct focus, the red spot and blue spot will coincide—be on top of one other.

One way to perform a surgical or therapeutic operation is to use a laser to ablate, cut, and/or cauterize tissue. In particular, very-short-pulse laser light (e.g., from one or more lasers that emit pulses shorter in duration than one nanosecond (typically called femtosecond pulses) concentrate power into a very short time period, such as are described in U.S. Patent Application Publications US 2004 0243111 A1 and US 2004 0243112 A1 by Mark Bendett et al., both of which are incorporated by reference) effects an ablation or tiny explosion that removes tissue with substantially no heating of surrounding or underlying tissue since the laser is turned off immediately after the extremely short pulse. In other embodiments, somewhat longer pulses and/or higher laser powers are used, and some heating and/or cauterization results. When a pulse train or series of such pulses are successively directed at a point, along a line or within an area, the tissue at that point, along that line or within that area is removed to a given depth. Further repetitions of pulses at the point, line, or area remove tissue to successively greater depths. The tissue-removing laser pulses act as an optical scalpel.

In some embodiments, it is desirable that the surgical or therapeutic operation be suppressed (inhibited or sufficiently reduced) to avoid damaging a nerve (e.g., to avoid damaging a facial nerve during an operation to remove a tumor). As used herein, "suppressed" includes both "inhibited" (meaning substantially stopped altogether) and "reduced" (meaning that the depth and/or lateral extent is reduced but not entirely inhibited). Using conventional methods, it is often difficult or cumbersome to locate particular nerves and/or to suppress the surgical or therapeutic operation when a nerve is located. Various embodiments of the present invention address these issues by sensing a result of stimulating a nerve (either a nerve action potential along the nerve at a short distance from the stimulation, or some other result such as a muscle twitch, or the like, caused by the nerve stimulation; still other embodiments directly stimulate a non-nerve tissue such as a muscle and sense that result), and then enabling the surgical operation (if it is desired to remove the tissue that reacted to the stimulation) or suppressing the surgical operation (if it is desired to preserve the tissue that reacted to the stimulation).

In some embodiments, the present invention provides an optical-electrical mechanism to stop the surgical laser pulses and/or reduce their power when the stimulation laser(s) and nerve sensor(s) detect a nerve, in order to preserve the nerve (if possible) while still removing other tissue as needed. In other embodiments, the surgery is performed by a mechanical scalpel (e.g., one that is robotically assisted or controlled, and the optical nerve stimulation and sensing is used to control movement and/or cutting of the mechanical scalpel to prevent or minimize nerve damage.

In some embodiments, a local anesthetic and/or analgesic 404 (e.g., such as novacaine or acupuncture; see FIG. 4A) can be administered "upstream" (e.g., between the surgical site and the brain) along a sensory nerve to prevent pain and discomfort during the operation, while the nerve stimulation and sensing of the present invention is still functional to locate and preserve the nerve at the site of the operation.

In some embodiments, the nerve simulation and sensing and the control of the optical scalpel is performed in "real time" in that the surgeon activates the cutting function and the stimulation/sensing functions, and manually moves the optical scalpel along a line, with a visible pointer laser indicating the location of where both stimulation and cutting would occur. As the optical scalpel is moved across or along a nerve that is stimulated by the stimulation laser, the sensing apparatus (e.g., a hook probe attached along the nerve) senses when the nerve is stimulated, and inhibits the cutting function until the optical scalpel has been moved off the nerve, whereupon the inhibition ceases and cutting again commences. In some such embodiments, the stimulation and sensing functions are used alone to determine a suitable location (e.g., perhaps at the junction of the ophthalmic, maxillary and mandibular branches of the trigeminal sensory nerve of the face) on the patient for placing each of one or more sensing probes. After the sensing probes are in place, the cutting function can be activated, and the sensing of nerve response would inhibit the cutting function to protect the sensed nerve. In some embodiments, a combination of "upstream" sensing-nerve sensors and "downstream" motor-nerve sensors are used to protect both types of nerves within the surgical area. In some embodiments, one or more stimulation pulses are alternated with one or more cutting pulses, such that the stimulation and sensing is done immediately before cutting is attempted, and if a nerve response is sensed, the cutting operation is suppressed.

Again, as used herein, "suppressed" includes both "inhibited" (meaning substantially stopped altogether) and "reduced" (meaning that the depth and/or lateral extent is reduced but not entirely inhibited). Typically, if a single nerve is stimulated, the response is either all (an action potential is triggered since the stimulation reached a threshold) or nothing (either no stimulation or a failed initiation where threshold is not reached and no action potential is propagated), while if an entire nerve bundle is stimulated, the signal strength can vary between a weak signal and a strong signal depending on the number of neurons that reached threshold. In some embodiments, any sensed reaction to nerve stimulation will inhibit or very strongly reduce the cutting depth (and/or lateral extent). In other embodiments, a strong sensed reaction to nerve stimulation will inhibit or strongly reduce the cutting depth (and/or lateral extent of the tissue removal), while weaker sensed reaction to nerve stimulation will reduce the cutting depth based on the strength of the sensed signal, providing a variable cutting based on how far from the nerve the cutting will occur or how large is the nerve bundle (e.g., sometimes allowing cutting or damage to small nerves while preventing damage to larger nerves).

In some embodiments, the surgical area is defined by a mask or marked boundary outside of which the cutting function is inhibited. For example, in some embodiments, the area to be treated is delineated by a marked line or shading (e.g., ink or a fluorescent dye) that indicates where cutting is permitted, and only when the visible pointer beam is projected on the allowed area is the cutting beam activated, but when the pointer is outside the allowed area, the cutting is inhibited. This additional inhibition function provides an additional safeguard as to where cutting is performed.

In other embodiments, rather than real-time stimulation sensing and inhibition, these functions are temporally separated, such that the sensing function is used first to create a map of the nerve locations, and later the inhibition functions are controlled by that map. For example, in some embodiments, the optical stimulation and the sensing are used to locate points along the various nerves within the planned surgical area. In some embodiments, these nerves are delineated by marked lines or shading (e.g., ink or a fluorescent dye) that indicate where cutting is or is not permitted. In other embodiments, one or more video cameras are connected to a computer and used to provide the location of the pointer laser when a response is sensed, and these locations are recorded into the computer's memory (e.g., optionally using fiducial marks or facial features as references for the map), and a computer-generated light map defining the nerve locations is projected (e.g., by a computer-projector display) onto the patient's tissue (e.g., the face). This map is then used to guide the cutting operation, both showing the surgeon where the nerves are located and/or as cut-inhibiting references that are sensed by the computer's video camera(s) such that when the pointer laser is on or next to a previously located nerve (as indicated by the proximity of the laser-pointer light to the projected nerve location), the cutting function is inhibited.

Figure 4A:
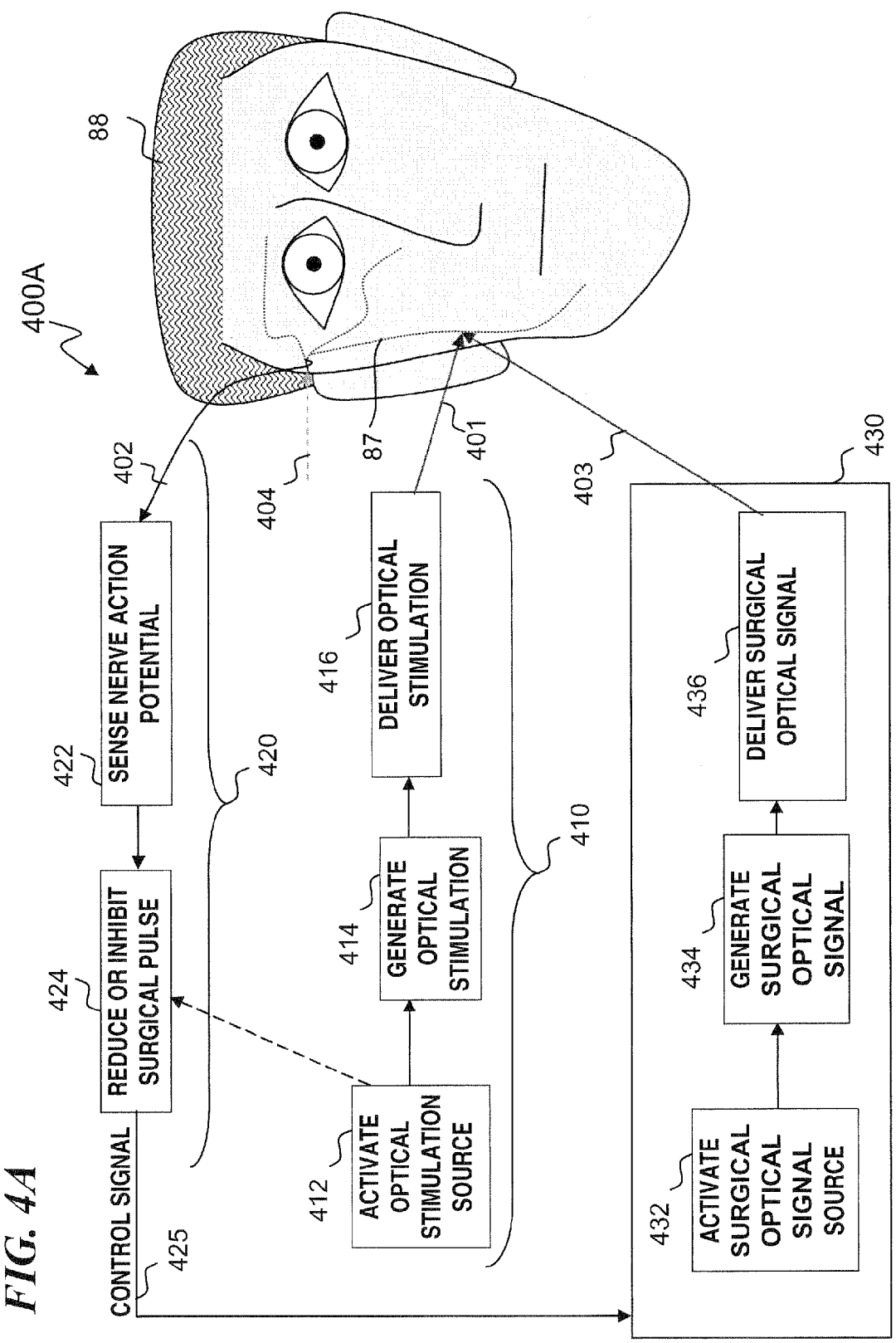
FIG. 4A is a block diagram of surgery-inhibiting nerve-stimulation system 400A.

FIG. 4A is a block diagram of surgery-inhibiting nerve-stimulation system 400A. In some embodiments, system 400A stimulates a tissue of patient 88 using an optical signal 401 focussed to a suitably small tissue area and a suitable tissue depth. If a sensory nerve 87 (and/or a motor nerve) is stimulated by the optical stimulation signal 401 (e.g., a laser signal pulse having an IR wavelength of about 1.8 microns, in some embodiments) sufficiently to trigger an action potential (e.g., a CNAP), that nerve stimulation is sensed (e.g., by the nerve's electrical signal sensed by a needle-sized hook probe or other suitable probe along the stimulated nerve a short distance away (e.g., towards the brain if the nerve is a sensory nerve, or towards the muscle if the nerve is a motor nerve), or by a mechanical sensor such as a small piezo sensor or strain gauge that outputs an electrical signal if the muscle twitches due to the nerve being stimulated) and if sense signal 402 indicates the nerve was stimulated, then surgical or therapeutic operation 403 is suppressed (inhibited or sufficiently reduced) to avoid damaging the stimulated nerve 87.

For example, in some embodiments, the stimulation signal is formed and/or focussed onto the patient's tissue to a stimulation spot diameter of 0.1 mm or smaller to a spot diameter of 2 mm or larger, although various embodiments use spot diameters of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.2 mm, about 2.4 mm, about 2.6 mm, about 2.8 mm, about 3.0 mm, about 3.2 mm, about 3.4 mm, about 3.6 mm, about 3.8 mm, about 4.0 mm, about 4.2 mm, about 4.4 mm, about 5.6 mm, about 4.8 mm, or about 5.0 mm, or over about 5 mm; in some embodiments, the spot is circular while in other embodiments, the spot is elongated to an oval, a rectangle or a short line and a suitable tissue depth (e.g., in some embodiments, to a stimulation depth of about 0.6 to 0.7 mm; in other embodiments, to a stimulation depth 0.1 mm or shallower to a stimulation depth of 2 mm or deeper, although various embodiments use stimulation depth of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, or deeper than 2 mm).

Referring again to FIG. 4A, in some embodiments, system 400A includes a stimulation unit 410 that outputs an optical signal that is effective at stimulating a nerve 87 of patient 88. In some embodiments, stimulation unit 410 includes block 412 (e.g., a trigger such as 108A of FIG. 1A described above) that activates an optical stimulation source, block 414 (e.g., an IR laser diode such as device 151 of FIG. 1A described above) that generates an optical stimulation signal, and unit 416 (such as an optical fiber and/or lens system that directs and/or focuses optical signal 401 onto a particular location with desired characteristics (such as size, power, shape, and the like) to stimulate nerve 87). In some embodiments, a suitable probe (such as a needle hook adapted to attach to an empirically determined location on nerve 87 to detect whether an action potential has been triggered) generates a relatively small signal that is amplified and/or conditioned by block 422 (e.g., a sensitive low-current differential operational amplifier circuit) and block 424 (e.g., an analog and/or digital logic circuit that examines the output signal from block 422 in relationship to the stimulation trigger from block 412 to determine whether to reduce or inhibit the surgical signal and/or by how much to reduce the cutting signal) that generates control signal 425. In some embodiments, control signal 425 controls one or more aspects of block 430, which is what generates and/or controls the surgical optical pulses 403. In some embodiments, stimulation optical signals 401 and/or surgical optical signals 403 also include a visible pointer signal to show the user where the stimulation and/or surgery is taking or is soon to be taking place, and optionally the stimulation signal, the visible pointer, and the cutting optical signal are all generated from a single unit (e.g., an optical unit such as unit 111 of FIG. 1D) and/or are all combined and delivered through a single output lens and/or optical fiber. In some embodiments, block 430 is implemented as a separate laser and controller (e.g., such as a LASIK opthalmic surgical optical source (Laser-Assisted In Situ Keratomileusis, using an excimer laser)) whose output is controlled and/or inhibited by control signal 425, and delivered by an optical fiber or combined into a single optical fiber with the stimulation signal 401 for delivery and placement onto the surgical site on patient 88. In other embodiments, a single hand-held self-powered (e.g., via internal batteries or other power source 150, as shown in the figures above) stimulation and surgical laser handpiece is implemented and the cutting operation is controlled and/or inhibited by control signal 425 generated by an integrated or by a separate sensing and inhibition unit 420 (e.g., in some embodiments, system 400A is implemented and contained in a single handpiece such as 140E of FIG. 1E described above).

In various embodiments, the sensing, inhibition and/or control functions of sensing and inhibition unit 420 are used in combination with or integrated into any of the nerve-simulation systems described herein or described in U.S. patent application Ser. No. 11/257,793 filed on Oct. 24, 2005, entitled "APPARATUS AND METHOD FOR OPTICAL STIMULATION OF NERVES AND OTHER ANIMAL TISSUE" (which is incorporated herein by reference, and which is now U.S. Pat. No. 7,736,382 titled "APPARATUS FOR OPTICAL STIMULATION OF NERVES AND OTHER ANIMAL TISSUE").

Figure 4B:
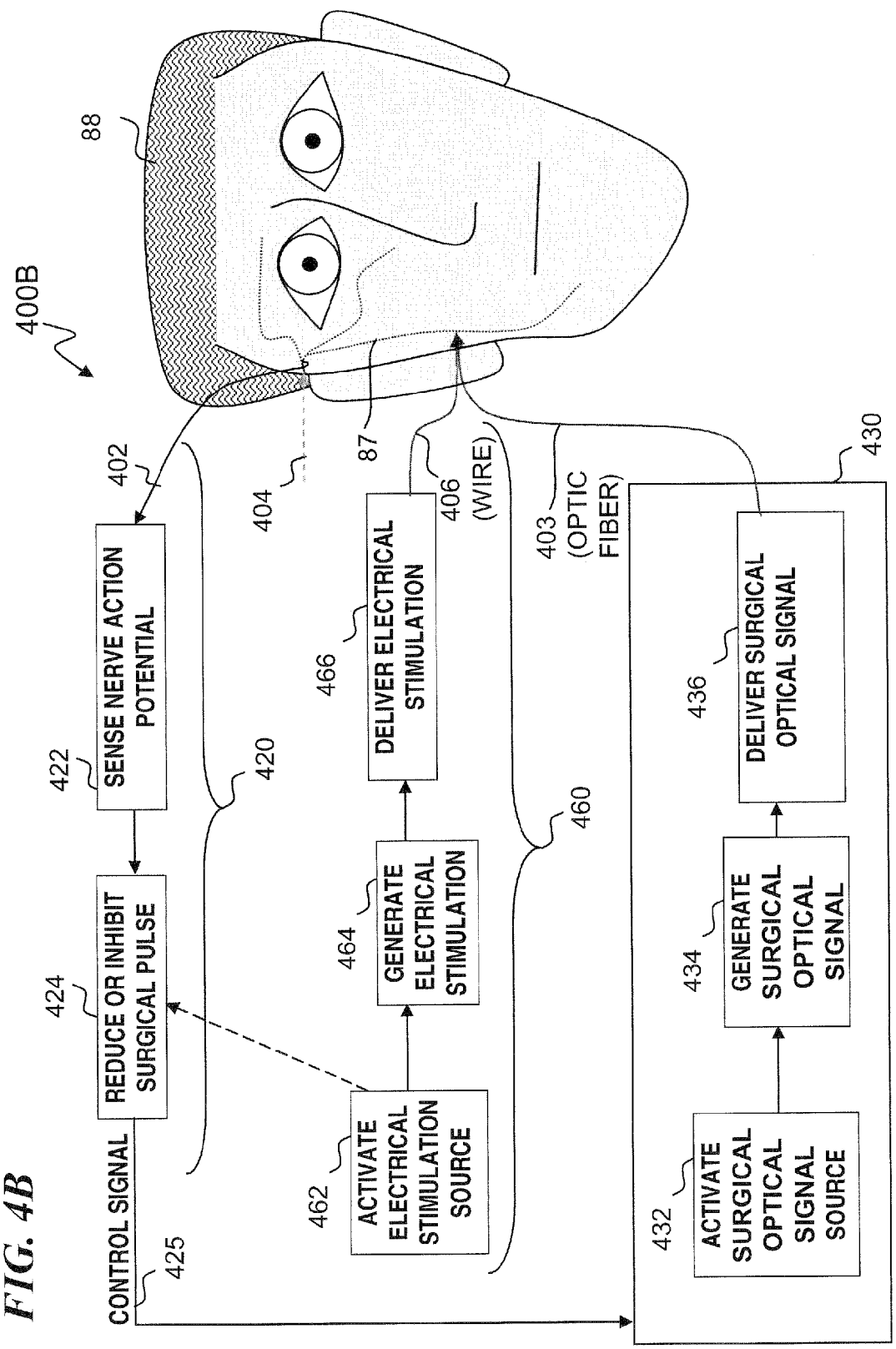
FIG. 4B is a block diagram of surgery-inhibiting nerve-stimulation system 400B.

FIG. 4B is a block diagram of surgery-inhibiting optical-signal nerve-stimulation system 400B. In some embodiments, the sensing, inhibition and/or control functions of sensing and inhibition unit 420 are used in combination with or integrated into a conventional electrical nerve stimulation unit 460 such as a conventional electrical-based electromyography (EMG) machine as is commonly used for nerve-conduction studies. In some embodiments, block 462 (e.g., a trigger corresponding to block 412 of FIG. 4A described above) activates an electrical stimulation source, block 464 (e.g., corresponding to block 414 of FIG. 4A described above) that generates an electrical stimulation signal, and unit 466 (such as a wire or needle along a side of the optical fiber, or an electrical conductor or sheath on the optical fiber that directs and/or focuses optical signal 403 onto a particular location with desired electrical characteristics (such as voltage, current, temporal shape, and the like) to stimulate nerve 87), wherein an electrical signal 406 is delivered by the electrical conductor (e.g., wire) to stimulate tissue next to the delivery end of the optical fiber that delivers optical surgical laser pulses 403, and the sensing and inhibition unit 420, when a nerve signal is sensed (a nerve signal initiated by electrical stimulation from the needle above), inhibits or reduces the power to the optical pulses 403 used for cutting/ablation.

Figure 4C:
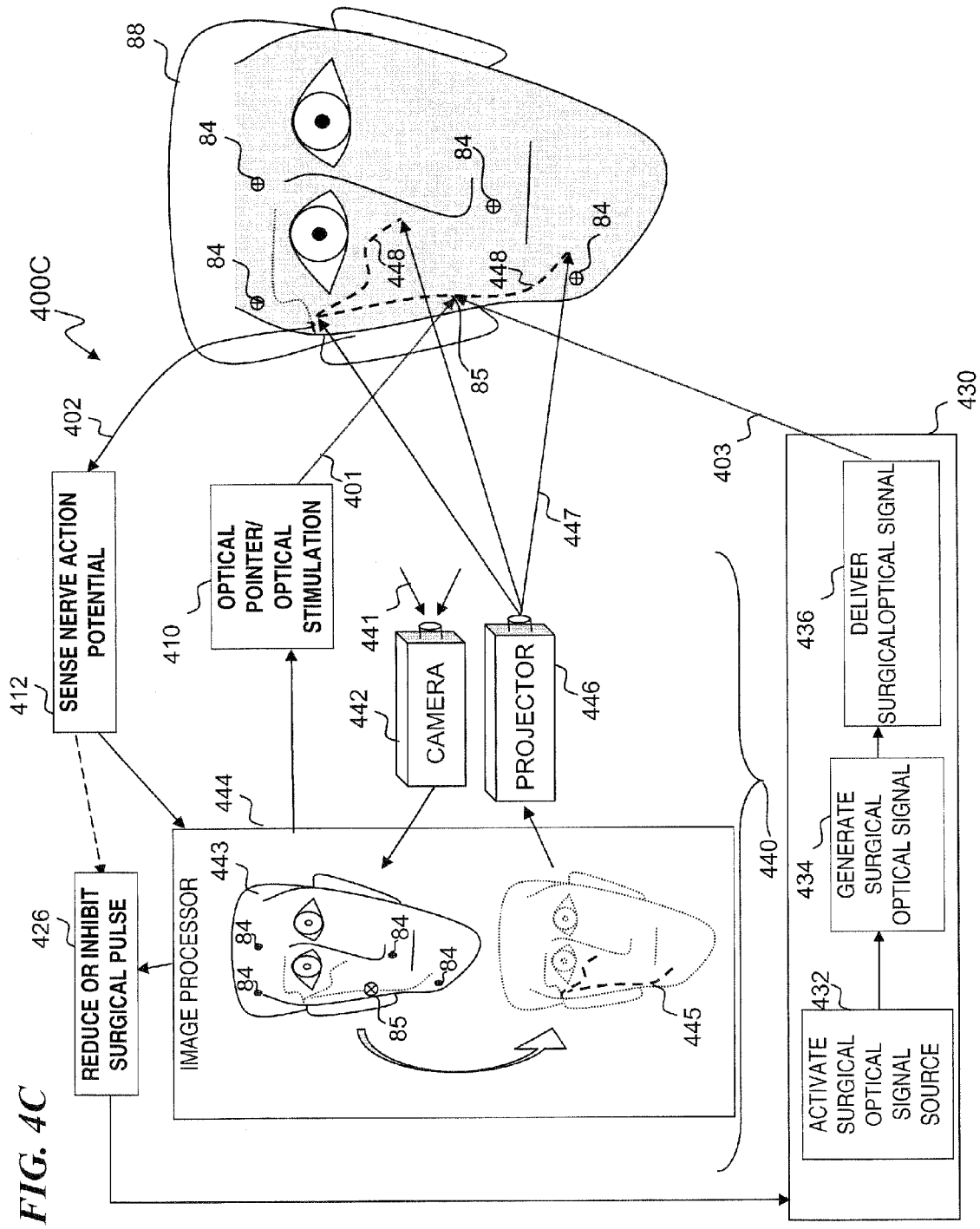
FIG. 4C is a block diagram of surgery-inhibiting nerve-stimulation system 400C.

FIG. 4C is a block diagram of surgery-inhibiting optical-signal nerve-stimulation system 400C. In some embodiments, system 400C is the same as system 400A of FIG. 4A described above, but with the addition of a camera and projector mapping system 440 that detects the locations of one or more nerves, optionally projects a map of the located nerves, and suppresses output from the cutting laser when in the vicinity of the detected and mapped nerves. In some embodiments, camera and projector mapping system 440 includes a camera 442 that gathers light 441 from the patient 88 and forms a digital image 443. In some embodiments, fiducial marks 84 (e.g., crosses drawn by an ink pen) are placed on the patient 88 and are detected on digital image 443 by image processor 444 (e.g., a combination of hardware and software, in some embodiments). The location 85 of the visible pointer laser (part of signal 401) from optical pointer/optical stimulation unit 410 is also located by image processor 444 from image 443. By correlating the location 85 on image 443 relative to fiducials 84 (or relative to other features of the image) at the moment that a nerve reaction is sensed in signal 402 by sensing circuit 412 and transmitted to image processor 444, a map 445 of the location(s) of nerve(s) on the patient is generated by image processor 444. In some embodiments, map 445 is also projected onto patient 88 as a projected pattern 447 from projector 446 that is visible as projected map 448 of the one or more nerves. The map that results can be used a short time later (e.g., a matter of seconds or minutes later, or even hours later) in combination with the detected location cutting signal 403 (either by camera 442 being sensitive to the wavelength of the cutting signal 403, or by including a visible laser signal that is coincident with cutting signal 403 and which is thus detectable by camera 442) to activate the inhibiting/control circuit 426 (similar in output to circuit 424 described above for FIG. 4A), which then suppresses the cutting portion of signal 403. This configuration of FIG. 4C is particularly useful when the nerve reaction time to stimulation is slow relative to the movement speed of the cutting optical implement 430, such that real-time sensing and inhibition is impractical. System 400C can be used to map the location of the nerves at a speed compatible with the nerve reaction and conduction times, and the map 445 can then be used to suppress (inhibit or reduce, as desired) the cutting beam. Note that in some embodiments, the map 445 need not be projected onto the patient (i.e., projector 446 can be omitted), but its data on the nerve locations can still be used to inhibit cutting in the locations of the mapped nerves.

FIG. 4D is a block diagram of surgery-inhibiting nerve-stimulation system 400D. System 400D is similar to system 400A described above for FIG. 4A, except that the handheld self-contained stimulation unit 140B (such as unit 140B of FIG. 1B described above) is physically separate from hand-held self-contained surgical unit 480B (similar to unit 140B of FIG. 1B described above, except that a surgical-ablation laser (one that outputs femtosecond-type pulses capable of ablating very small pieces of tissue) replaces the stimulation laser). In some embodiments, a wireless transceiver-controller 109B (e.g., part of a unit such as unit 141 of FIG. 1B) transmits control signals to handpiece 140B and also indicates the timing of those pulses to inhibiting/control logic 424. If the differential sensing amplifiers (op amps) 422 detect a nerve-action-potential caused reaction (e.g., a nerve twitch sensed by skin-mounted motion sensors (as are well known in the art) or galvanic skin response sensors (e.g., such as are used in polygraph truth detectors, also well known in the art)), the resulting signal to response-sensing, surgery-inhibiting logic 424 sends a control signal 425 to wireless transceiver-controller 409B, which transmits an inhibit signal via its wireless linkage to handpiece 480B, and the cutting signal is reduced and/or inhibited based on the sensed signal. In other embodiments, the functions of both handpieces 140B and 480B are combined into a single handpiece having a combination of some or all of the above-described functions. In some embodiments, the wireless transceiver-controller 409B and/or wireless transceiver-controller 109B also have trigger signal inputs so a user can use a remote control (such as one or more foot-activated switches to activate their respective functions.

FIG. 5A is a perspective cut-away diagram of a surgery-inhibiting nerve-stimulation system 500 at the initiation of a surgical procedure. In some embodiments, hand-held laser stimulation/surgical device 540 includes a plurality of light-emitting functions including emitting an optical nerve-stimulation signal, a visible optical pointer signal, and/or an optical surgical ablation signal, and also includes a surgical suppression function as described above for FIGS. 4A-4D. In some embodiments, hand-held laser stimulation/surgical device 540 is scanned back and forth (e.g., in a raster pattern) and projects optical stimulation light onto the skin of patient 88, with any nerve-reaction signal (i.e., as a result of the optical stimulation) that is detected sending a signal along wire 402 to inhibit the surgical function of stimulation/surgical device 540. If no nerve-reaction signal is detected, the surgical function of laser stimulation/surgical device 540 is activated, with a resulting surgical operation being performed (e.g., ablation of the thin layer of tissue that has been stimulated with no ensuing nerve-reaction signal being detected). In some embodiments, the nerve-stimulation signal is one or more pulses that are projected, and if no suppression signal is generated, one or more ablation light-signal pulses are emitted, and the process of this sentence is iteratively repeated as the handpiece is moved across the tissue surface.

In some embodiments, the stimulation function of laser stimulation/surgical device 540 penetrates about 0.6 mm, and is not sufficiently intense to stimulate nerve 87 that lies below that depth in patient 88's tissue. In some embodiments, laser stimulation/surgical device 540 is configured to be moved back and forth across patient 88's skin manually. In other embodiments, laser stimulation/surgical device 540 is moved back and forth across patient 88's skin automatically (e.g., being controlled by a programmed computer-control system). In some embodiments, the surgeon marks the patient's skin (e.g., with a pen line 544 on the patient's skin or with white tape that masks the area outside line 544, or the like) to delineate the area where surgery is allowed, and surgery-area boundary marking 544 is used as a predetermined boundary marking that limits the travel excursion of laser stimulation/surgical device 540 (or inhibits its surgical light output) in computer-controlled embodiments. Surgery-area boundary marking 544 may also be a predetermined boundary marking that serves as a guide to limit the manual travel excursion of laser stimulation/surgical device 540 (or inhibits its surgical light output) in manually controlled embodiments.

FIG. 5B is a diagram of a first stimulation/surgical pattern 542 at an operation site at which a surgery-inhibiting nerve-stimulation system is employed, at a first time subsequent to the initiation of a surgical procedure. Laser stimulation/surgical device 540 (see FIG. 5A) passes back and forth across patient 88's skin, along pattern 542 that is limited by surgery-boundary marking 544. In some embodiments, the surgical light output from handpiece 540 ablates to a small depth on each pass, and deeper tissue removal is accomplished by repeated passes. Since no nerve stimulation was detected in this embodiment so far (since the nerves are located deeper than the stimulation penetration), the cutting/tissue ablation signal is not inhibited (note the continuous dark lines for pattern 542), and a uniform tissue removal is accomplished within boundary 544.

FIG. 5C is a diagram of a surgical site at which a surgery-inhibiting nerve-stimulation system is employed, at a time when the stimulation/surgical pattern shown in FIG. 5B has been completed. Tissue has been surgically removed by laser stimulation/surgical device 540 to a shallow depth 546 and to lateral boundary 544.

FIG. 5D is a diagram of a second stimulation/surgical pattern at an operation site at which a surgery-inhibiting nerve-stimulation system is employed, at a second, later time subsequent to the initiation of a surgical procedure, and showing the surgical site at a time when the second stimulation/surgical pattern has been completed. Manual or computer-controlled passing of laser stimulation/surgical device 540 across patient 88's body within boundary 544 ablates-away further tissue to a depth 547 where no nerve has been stimulated. However, where the stimulation function of laser stimulation/surgical device 540 has resulted in stimulation of a nerve and a nerve reaction has been detected (e.g., by hook probe 402, in some embodiments) as the stimulation signal hits and triggers a nerve response with a resulting action-potential signal being detected and directed along wire 402 (see FIG. 5A), the surgical function of laser stimulation/surgical device 540 is suppressed (note the light dotted lines above the nerves where ablation is suppressed, but the dark lines in other areas where ablation is not suppressed), resulting in non-ablation of nerve 87; the top of non-ablated nerve 87 is at depth 541.

FIG. 5E is a diagram of a third stimulation/surgical pattern at an operation site at which a surgery-inhibiting nerve-stimulation system is employed, at a third, later time subsequent to initiation of a surgical procedure, and showing the surgical site at a time when the third stimulation/surgical pattern has been completed. Further non-nerve tissue has been ablated away to a depth 548 within boundary 544, however, nerve 87 is again not ablated by laser stimulation/ surgical device 540—the nerve having been stimulated by the stimulation function, with a signal resulting from detection of a nerve reaction passing up wire 402 and inhibiting the surgical function. The top of non-ablated nerve 87 remains at depth 541.

FIG. 5F is a diagram of an operation site at which a surgery-inhibiting nerve-stimulation system is employed, when the operation has been completed. Non-nerve tissue has been ablated or otherwise surgically removed to a depth 549 within boundary 544. But again, nerve 87 has not been ablated by laser stimulation/surgical device 540—the nerve having been stimulated by the stimulation function, with a signal resulting from detection of a nerve reaction passing up wire 402 and inhibiting the surgical function. The top of non-ablated nerve 87 remains at depth 541. In this way, unwanted tissue (e.g., a tumor) can be removed while preserving at least some of the nerves passing through the surgical site.

In some embodiments, an imaging optics turret (such as described in U.S. patent application Ser. No. 11/257,793 filed on Oct. 24, 2005, entitled "APPARATUS AND METHOD FOR OPTICAL STIMULATION OF NERVES AND OTHER ANIMAL TISSUE" which is incorporated herein by reference, and which is now U.S. Pat. No. 7,736,382 titled "APPARATUS FOR OPTICAL STIMULATION OF NERVES AND OTHER ANIMAL TISSUE") is provided at the operative end of handpiece 140 (with any letter suffix following the "140") of the present invention, such that different optical patterns, spot sizes, and/or focal lengths can be provided by selecting one of a plurality of different lenses or holographic imagers (e.g., a turret that can be rotated to select one imaging optical element of the plurality of imaging optics). In other embodiments, a zoom-type lens is provided such that spot size and/or shape and focal length can be independently changed.

In some embodiments, a plurality of manually or foot-activateable trigger buttons and corresponding wireless connections, mechanical linkages, electrical connections, or other connectivities, are provided to select and/or activate one or more of a plurality of different functions of the handpiece, as described below. In other embodiments a voice-activated switch or other activation means is used instead of or in addition to manually activated or foot-activated buttons.

In other embodiments, the mechanical linkage(s) and trigger(s) are omitted and replaced with a non-magnetic optical-fiber-connected controller-selector that is manually operable to select and/or activate one or more functions. In still other embodiments, a foot-operated control is used instead.

In some embodiments of the mechanically-linked or optical-fiber-connected manual or foot controls (or a similarly functional foot control), three buttons are provided: a first button that when pushed a first time starts a series of one or more optical pulses, which series of one or more optical pulses optionally can automatically stop after a period of time determined by the function selected, or optionally can stop only after the user presses this first button a second time; a second button that, when pressed, advances a function-selecting state machine to the next one of a plurality of different optical-stimulation functions (e.g., no stimulation function is selected, or selecting the duration, intensity, pulse rate, pulse shape, pulse-train shape or pattern, and/or wavelength(s), and the like, for the IR stimulation light), wherein these functions are activated and/or deactivated by pressing the first button; and a third button that, when pressed, advances a state machine to the next one of a plurality of different optical-surgery functions (e.g., no surgical function is selected, or ablation, cutting, cauterizing, and the like functions for the high-powered laser light) that are activated and/or deactivated by pressing the first button. In some embodiments, successive presses of the stimulation or surgery function-selection buttons cycle through each of the items on the menu(s) of functions available.

In some embodiments, a single actuation/control button 108 is used both to select a stimulation function (e.g., by successive single long-duration presses of button 108 to select different functions as shown, e.g., in FIG. 1F) and to control triggering or timing of the stimulation light (e.g., by a quick double-click of button 108).

In some embodiments, upon changing the stimulation and/or surgery function by pressing of the respective function-selection buttons, the color of the visible light being sent down the optical fiber changes to a different color (e.g., hue, saturation, and/or intensity) and/or pulse (brightness pulsations) pattern, wherein the visible light color and/or pulsing of the light intensity is indicative of the function selected, thus providing instant feedback to the user concerning which function is currently active. For example, in some embodiments, a steady light of one of a plurality of different colors indicates that a stimulation function has been selected, wherein the color indicates which of the stimulation functions has been selected; whereas a quickly pulsating light of one of a plurality of different colors (also different than the stimulation-indicating colors) indicates that a surgery function has been selected, wherein the color of the pulsing light indicates which of the surgery functions has been selected. In some embodiments, audio feedback is also provided as the selection buttons cycle through the menus of functions available (such as a synthesized or recorded voice or a set of distinctive tones that announces which function has been selected).

In some embodiments, handpiece 140 is controlled using a manually controlled selector implementing a finger or thumb control (such as described in commonly owned U.S. patent application Ser. No. 11/257,793 filed on Oct. 24, 2005, entitled "APPARATUS AND METHOD FOR OPTICAL STIMULATION OF NERVES AND OTHER ANIMAL TISSUE", incorporated herein by reference, which is now U.S. Pat. No. 7,736,382 titled "APPARATUS FOR OPTICAL STIMULATION OF NERVES AND OTHER ANIMAL TISSUE") for local mechanical control of the stimulation light. In some embodiments, a shutter is operated by button (in other embodiments, a user-controlled variable iris is provided instead of or in addition to shutter). In some embodiments, a turret having a plurality of different lenses (e.g., having different focal lengths, spot sizes, and/or cylinder/astigmatism (to focus to a long narrow spot or line on the nerve), neutral-density filters, holographic imagers or other optics) is rotatable using ratchet-pawl operated by button.

In some embodiments of any of the Figures and descriptions herein, a thin transparent membrane (such as plastic surgical tape or sterilized Saran Wrap™) is placed over and/or in contact with the nerve to keep it from drying out (again, drying can cause tissue damage and changes the reflectivity to the stimulation light signal). Some embodiments of the invention use a method of stimulating and/or treating nerves that includes covering the nerve with a transparent material (which is either flexible membrane or rigid substrate, or a combination of the two, depending on the embodiment), and delivering an efficacious amount of light through the transparent material. In some embodiments, the transparent material is configured to prevent drying. In some embodiments, the transparent material is configured to ensure a proper focus of the light. In some embodiments, the material is partially transparent, in order to reduce the intensity of the delivered light signal by a predetermined amount. In other embodiments, the material is substantially fully transparent, in order to deliver a maximum amount of light.

In some embodiments, the pattern and speed of scanning is predetermined by a computer program, while in other embodiments the pattern is manually controlled by operator 89. In some embodiments, the computer program controls the emission of stimulation laser light in some type of spatial and/or temporal pattern based upon an algorithm (e.g., a programmed binary search, sequential search, or the like) so as to determine which stimulation area delivered an efficacious dose of IR light to the nerve of interest.

The actual reaction or response of nerve tissue to IR-light stimulation would, in some embodiments, be determined through empirical observation (muscle twitches), subject reporting (of a touch sensation, taste sensation, or other sensation). In some embodiments, the user changes the position and/or function (e.g., changing the pulse length or intensity) of the handpiece based on the response. In other embodiments, the response is detected by the stimulation system, and the function of the stimulation system automatically adjusts the stimulation based on the response feedback (e.g., in some embodiments, a stimulation signal is repeated until the response is detected, and then the stimulation stops and/or an audio or visual indication of the response is output by the stimulation system). The manipulation of the array head itself is facilitated, in, at least one embodiment, through the use of an ergonomically designed handle, which is covered by a replaceable, disposable, sterile sheath, and by the feedback to the user provided by having visible light delivered to the area that would be stimulated by the IR stimulation signal and/or the other audio and/or visual indications.

In some embodiments, a high-power laser is also coupled to the optical fiber (or carried in its own separate fiber), in order to provide a capability for cutting or ablating tissue (e.g., nerve or brain tissue that has been located and identified by the light stimulation signals). This allows the surgeon to stimulate a brain area (or other nerve tissue) to more precisely locate specific regions that are to be saved versus other areas that are to be cut, cauterized or ablated. Thus, a surgeon wanting to excise a tumor or an epileptic focus can better locate and identify, e.g., borders of a lesion and surrounding functional portions of the brain using the optical-fiber-delivered optical stimulation according to the present invention, and then use the optical-fiber-delivered cutting or ablating function.

As used herein, the "launch end" on an optical fiber is not limited to just the fiber's first end, but can also be the point or length along the fiber to which light from a source (such as a laser diode) is coupled to insert the light into the fiber, and the "delivery end" is not limited to just the fiber's second end, but can also be the point or length along the fiber from which light from the fiber is ejected to illuminate and/or stimulate a nerve or neural tissue.

In some embodiments, action potentials are all-or-none, binary occurrences and therefore are not reinforceable—once an action potential is triggered, it goes to the end of the axon and causes neurotransmitter release into the synaptic cleft. However, if a nerve is cut or damaged by disease, it may be desirable to start an action potential and then restart the action potential beyond the damaged area.

In some embodiments, a set of machine control instructions (programmable control code to adjust, time, or otherwise control pulse shape, timing, intensity, and the like) is stored on computer-readable medium (for example, a compact FLASH memory fob, diskette, CDROM, or network connection (e.g., the internet)), which is connectable to control one or more operations or functions of the light-emitting-source controller.

In some embodiments, one or more of the items labeled herein as "plastic" are implemented using some other non-magnetic material such as ceramic or structured carbon nanotubes, or the like. In other embodiments, one or more of the items labeled herein as "laser diodes" are implemented instead as light-emitting diodes (LEDs) or as optically-pumped solid-state optical amplifiers (e.g., semiconductor laser-like devices that are pumped optically).

In some embodiments, a kit containing various components is included, this kit containing a first light-emitting source, a second light-emitting source, a light-beam combiner, a mechanical linkage with a trigger mechanism, a light-emitting-source controller, and a disposable sheath. Also contained in this kit are the various materials needed to assemble the apparatus.

In some embodiments, a single pulse of light is emitted based on a manual user input (such as the press of a button or the rolling of a wheel) that is coupled mechanically, electrically or optically to the light-emitting-source controller (e.g., a unit that applies electrical power to a laser diode).

In some embodiments, a pulse train of light is emitted based on a manual user input (such as the press of a button or the rolling of a wheel) that is coupled mechanically, electrically or optically to the light-emitting-source controller (e.g., a unit that applies electrical power to a laser diode).

In some embodiments, a shaped, non-square pulse of light is emitted based on a manual user input (such as the press of a button or the rolling of a wheel) that is coupled mechanically, electrically or optically to the light-emitting-source controller (e.g., a unit that applies electrical power to a laser diode).

In some embodiments, a shaped pulse train of light is emitted based on a manual user input (such as the press of a button or the rolling of a wheel) that is coupled mechanically, electrically or optically to the light-emitting-source controller (e.g., a unit that applies electrical power to a laser diode).

Some embodiments of the present invention include an implantable apparatus that has an optical-light stimulator operable to generate a light signal that will stimulate a nerve, a first optical fiber operatively coupled to receive light from the stimulator and deliver the light to the nerve, a power source operatively coupled to power the stimulator, and a receiver configured to receive programming commands from a wireless remote programmer, in order to selectively control operation of the stimulator based on a set of data that was wirelessly received.

In some embodiments, the apparatus is configured to be implanted in the body of a mammal. In some embodiments, the power source is a battery. In some embodiments, the stimulator further includes an RF recharger operable to receive RF energy and recharge the battery. In some embodiments, the stimulator further includes a first light-emitting source and a second light-emitting source operatively coupled to be controlled by the stimulator. In some embodiments, the stimulator further includes an optical combiner operatively coupled to combine light from the first light-emitting source and the second light-emitting source into an optical fiber.

Some embodiments of the present invention include a method that includes charging a battery using RF energy, powering a controller from the battery, remotely programming the controller, selectively emitting light from a first light source under control of the controller, selectively emitting light from a second light source under control of the controller, combining the light from the first and second light sources, and transmitting the combined light to a nerve.

In some embodiments of this method, the selectively emitting light from the first light source includes emitting IR laser light from a laser diode. In some embodiments, the selectively emitting light from the second light source includes emitting visible light.

Some embodiments of the present invention include a kit that includes a first light-emitting source, a second light-emitting source, a light-beam combiner, a mechanical linkage with a trigger mechanism, a light-emitting-source controller, and a disposable sheath.

Some embodiments of the present invention include an apparatus that includes an optical fiber, an optical-fiber holder operable to optically couple the optical fiber to a nerve, and an optical sensor operable to distinguish nerve tissue from other tissue based on a sensed optical color.

Some embodiments further include one or more additional optical fibers, wherein an illumination light is delivered to the nerve tissue using one or more of the plurality of optical fibers and the sensed optical color is sensed through one or more of the optical fibers.

Some embodiments of the present invention include a method that includes generating light from a first laser-diode device, the light having a wavelength between about 1.8 microns and about 2.2 microns, and stimulating a nerve with the light. In some embodiments, the light from the first laser-diode device is in a range of between about 1.80 microns and about 1.85 microns, or in a range of between about 1.81 microns and about 1.86 microns, or in a range of between about 1.82 microns and about 1.87 microns, or in a range of between about 1.83 microns and about 1.88 microns, or in a range of between about 1.84 microns and about 1.89 microns, or in a range of between about 1.85 microns and about 1.90 microns, or in a range of between about 1.86 microns and about 1.91 microns, or in a range of between about 1.87 microns and about 1.92 microns, or in a range of between about 1.88 microns and about 1.93 microns, or in a range of between about 1.89 microns and about 1.94 microns, or in a range of between about 1.90 microns and about 1.95 microns, or in a range of between about 1.91 microns and about 1.96 microns, or in a range of between about 1.92 microns and about 1.97 microns, or in a range of between about 1.93 microns and about 1.98 microns, or in a range of between about 1.94 microns and about 1.99 microns, or in a range of between about 1.95 microns and about 2.00 microns, or in a range of between about 1.96 microns and about 2.01 microns, or in a range of between about 1.97 microns and about 2.02 microns, or in a range of between about 1.98 microns and about 2.03 microns, or in a range of between about 1.99 microns and about 2.04 microns, or in a range of between about 2.00 microns and about 2.05 microns, or in a range of between about 2.01 microns and about 2.06 microns, or in a range of between about 2.02 microns and about 2.07 microns, or in a range of between about 2.03 microns and about 2.08 microns, or in a range of between about 2.04 microns and about 2.09 microns, or in a range of between about 2.05 microns and about 2.10 microns, or in a range of between about 2.06 microns and about 2.11 microns, or in a range of between about 2.07 microns and about 2.12 microns, or in a range of between about 2.08 microns and about 2.13 microns, or in a range of between about 2.09 microns and about 2.14 microns, or in a range of between about 2.10 microns and about 2.15 microns, or in a range of between about 2.11 microns and about 2.16 microns, or in a range of between about 2.12 microns and about 2.17 microns, or in a range of between about 2.13 microns and about 2.18 microns, or in a range of between about 2.14 microns and about 2.19 microns, or in a range of between about 2.15 microns and about 2.20 microns, or in a range of between about 2.16 microns and about 2.21 microns, or in a range of between about 2.17 microns and about 2.22 microns, or in a range of between about 2.18 microns and about 2.23 microns, or in a range of between about 2.19 microns and about 2.24 microns, or in a range of between about 2.20 microns and about 2.25 microns.

Some embodiments of the method further include conveying the light from the laser-diode device to the nerve using an optical fiber. In some embodiments, the laser-diode device includes a plurality of emitters, and the method further includes combining the light from at least two of the plurality of emitters into the optical fiber.

Some embodiments of the method further include affixing the optical fiber to a frame fixed in positional relationship relative to a patient. Some embodiments of the method further include remotely controlling a positioning of the light relative to the nerve.

Some embodiments of the present invention include an apparatus that includes a first disposable sheath that includes a first optical system configured to focus light into a first predetermined pattern that is efficacious to optically stimulate a nerve.

Some embodiments are supplied as a kit that further includes a second disposable sheath that includes a second optical system configured to focus light into a second predetermined pattern, different than the first, which is efficacious to optically stimulate a nerve.

Some embodiments of the present invention include an apparatus that includes a first light-emitting source operative to emit an optical signal at a first wavelength that is capable of directly stimulating a nerve of a patient; an optical-fiber structure having a first end and a second end; a light-beam coupler that is configured to direct light from the first light-emitting source into the first end of the optical-fiber structure; a light-emitting-source controller operatively coupled to the first light-emitting source and the second light-emitting source to selectively control light output thereof, and a light-delivery unit operatively coupled to the second end of the optical-fiber structure, wherein the light-delivery unit, the optical-fiber structure or both the light-delivery unit and the optical-fiber structure are configured to direct the optical signal onto neural tissue.

In some embodiments, the first light-emitting source emits infrared (IR) light from a laser diode.

Some embodiments further include a second light-emitting source operative to emit an optical signal at a second wavelength that is capable of directly stimulating a nerve, wherein the second wavelength is different than the first wavelength and has a different penetration depth into a given tissue, and wherein light at the first wavelength is applied to achieve a first tissue-penetration depth, and light at the second wavelength is applied to achieve a second tissue-penetration depth.

Some embodiments further include a second light-emitting source operative to emit an optical signal at a second wavelength that is capable of directly stimulating a nerve, wherein the second wavelength is different than the first wavelength and has a different penetration depth into a given tissue, and variable amounts of the first and second different wavelengths are applied simultaneously to achieve a tissue-penetration depth that is variable based on the intensities of the first and second wavelengths of light.

Some embodiments further include a third light-emitting source, wherein the third light-emitting source emits visible light, and wherein the light-beam combiner is operatively coupled to direct light from the third light-emitting source into the optical-fiber structure.

In some embodiments, the light-delivery unit includes a handpiece configured to be held by hand during delivery of the nerve stimulation, and the apparatus further includes a disposable sheath configured to cover at least a portion of the handpiece to provide a sterile covering.

Some embodiments further include a user-operable control mechanism operatively coupled to the controller to control a function of the controller, the control mechanism being configured to be operated in conjunction with the handpiece.

In some embodiments, the user-operable control mechanism is mounted on the handpiece, and configured to be hand operated by a user.

In some embodiments, the user-operable control mechanism is mechanically linked to the light-emitting-source controller.

In some embodiments, the light-delivery unit includes a frame configured to be affixed to the patient, and a moveable light-delivery head connected to the frame and configured to be changeably positioned to deliver light to one of a plurality of locations on the patient.

Some embodiments of the present invention include a method that includes obtaining, from a first laser diode, a first laser beam having a first wavelength that is capable of directly stimulating neural tissue; transmitting the first laser beam in an optical-fiber structure; imaging the first laser beam from the optical-fiber structure onto a location on the neural tissue for stimulation of the neural tissue; and obtaining user input and based on the user input, controlling the first laser beam. In some embodiments, the first laser beam has an infrared (IR) wavelength.

Some embodiments of the method further include obtaining a second laser beam having a second wavelength that is capable of directly stimulating a nerve, wherein the second wavelength is different than the first wavelength and has a different penetration depth into a given tissue; transmitting the second laser beam in the optical-fiber structure; applying light at the first wavelength to achieve a first tissue-penetration depth; and applying light at the second wavelength to achieve a second tissue-penetration depth.

Some embodiments further include obtaining a second laser beam having a second wavelength that is capable of directly stimulating a nerve, wherein the second wavelength is different than the first wavelength and has a different penetration depth into a given tissue; transmitting the second laser beam in the optical-fiber structure; and applying variable amounts of the first and second different wavelengths simultaneously to achieve a tissue-penetration depth that is variable based on the intensities of the first and second wavelengths of light.

Some embodiments further include obtaining a third light beam having a visible-light wavelength; transmitting the third light beam in the optical-fiber structure; and imaging the third light beam from the optical-fiber structure as an indication of where the first laser beam is directed.

Some embodiments further include providing a handpiece for manually directing the location of the imaged stimulation light; and covering at least a portion of the handpiece with a sterile cover.

In some embodiments, the obtaining user input includes coupling a control mechanism to a laser controller to control a function of the controller, wherein the control mechanism is configured to be operated in conjunction with the handpiece.

In some embodiments, the control mechanism is mounted on the handpiece, and the obtaining user input includes coupling a manual operation of the control mechanism by a user to control the first laser beam.

Some embodiments further include providing a handpiece for manually directing the location of the imaged stimulation light, wherein the obtaining user input includes coupling a user-operated control mechanism to a laser controller to control a function of the controller, wherein the control mechanism is separate from the handpiece and is configured to be operated such that operation of the control mechanism is independent of movement of the handpiece.

Some embodiments further include providing a light-delivery unit for directing the location of the imaged stimulation light, wherein the light-delivery unit includes a frame configured to be affixed to the patient, and a moveable light-delivery head connected to the frame; and positioning the light-delivery head to deliver light to one of a plurality of locations on the patient.

Some embodiments of the present invention include an apparatus that includes means for generating a first laser beam having a first wavelength that is capable of directly stimulating neural tissue of a patient, wherein light of the first wavelength has a first tissue-penetration profile; means for transmitting the first laser beam; means for imaging the transmitted first laser beam onto a location on the neural tissue for stimulation of the neural tissue; and means for obtaining user input and based on the user input, controlling the first laser beam.

In some embodiments, the means for generating the first laser beam includes a laser diode and means for controlling electrical power to the laser diode to control timing and intensity of the first laser beam.

Some embodiments further include means for visibly indicating a location on the patient at which nerve stimulation is to be obtained by application of the first laser beam.

Some embodiments further include means for generating a second laser beam having a second wavelength that is capable of directly stimulating neural tissue of a patient, wherein light of the second wavelength has a second tissue-penetration profile different than the first tissue-penetration profile, and wherein the means for generating the second laser beam is optically coupled to the means for imaging.

Some embodiments further include means for generating a third laser beam that is capable of optically cutting tissue, wherein the means for generating the third laser beam is optically coupled to the means for imaging.

In some embodiments, the apparatus is made of materials compatible with use within a magnetic field of an operating magnetic resonance machine.

Some embodiments of the present invention include an apparatus that includes an elongated endoscope structure having an image-obtaining end configured to be inserted into a small opening in a patient to enable viewing of an interior tissue of the patient; a first laser diode operable to output a laser beam having a first wavelength, and that is capable of directly stimulating neural tissue of a patient, wherein light of the first wavelength has a first tissue-penetration profile; a fiber holder operable to hold an optical fiber having a first end optically coupled to receive the laser beam from the first laser diode and configured to deliver the laser beam to a second end to stimulate neural tissue of the viewed interior tissue of the patient; and a user-input interface operable to obtain user input and based on the user input, to control application of the first laser beam.

Some embodiments further include the optical fiber.

In some embodiments, the fiber holder is further configured to implant and release the optical fiber in the patient.

Some embodiments include combinations of elements from different ones of the above-described Figures and specifications. Some embodiments of the invention include a computer-readable medium that has instructions stored thereon for causing a suitably programmed information processor to perform methods that include one or more of the functions or subfunctions described herein.

Some embodiments of the present invention include an apparatus that includes a first light-emitting source operative to emit an optical signal at a first wavelength that is capable of directly stimulating muscle tissue of a subject; an optical-fiber structure having a first end and a second end; a light-beam coupler that is configured to direct light from the first light-emitting source into the first end of the optical fiber structure; a light-emitting-source controller operatively coupled to the first light-emitting source to selectively control light output thereof, and a light-delivery unit operatively coupled to the second end of the optical-fiber structure, wherein the light-delivery unit, the optical fiber structure or both the light-delivery unit and the optical-fiber structure are configured to direct the optical signal onto muscle tissue. In some embodiments, the first light-emitting source emits infrared (IR) light from a laser diode.

Some embodiments of the muscle stimulator further include a second light-emitting source operative to emit an optical signal at a second wavelength that is capable of directly stimulating muscle tissue, wherein the second wavelength is different than the first wavelength and has a different penetration depth into a given tissue, and wherein light at the first wavelength is applied to achieve a first tissue-penetration depth, and light at the second wavelength is applied to achieve a second tissue-penetration depth.

Some embodiments of the muscle stimulator further include a second light-emitting source operative to emit an optical signal at a second wavelength that is capable of directly stimulating muscle tissue, wherein the first wavelength is different than the second wavelength and has a different penetration depth into a given tissue, and variable amounts of the first and second different wavelengths are applied simultaneously to achieve a tissue-penetration depth that is variable based on the intensities of the first and second wavelengths of light.

Some embodiments of the muscle stimulator further include a third light-emitting source, wherein the third light-emitting source emits visible light, and wherein the light-beam combiner is operatively coupled to direct light from the third light-emitting source into the optical-fiber structure.

In some embodiments of the muscle stimulator, the light-delivery unit includes a handpiece configured to be held by hand during delivery of the muscle tissue stimulation, and the apparatus further includes a disposable sheath configured to cover at least a portion of the handpiece to provide a sterile covering.

Some embodiments of the muscle stimulator further include a user-operable control mechanism operatively coupled to the controller to control a function of the controller, the control mechanism being configured to be operated in conjunction with the handpiece.

In some embodiments of the muscle stimulator, the user-operable control mechanism is mounted on the handpiece, and configured to be hand operated by a user. In some embodiments, the user-operable control mechanism is mechanically linked to the light-emitting-source controller. In some embodiments, the light-delivery unit includes a frame configured to be affixed to the subject, and a moveable light-delivery head connected to the frame and configured to be changeably positioned to deliver light to one of a plurality of locations on the subject.

Another aspect of some embodiments of the invention include a method that includes obtaining, from a first laser diode, a first laser beam having a first wavelength that is capable of directly optically stimulating an action potential in a tissue of an animal; transmitting the first laser beam in an optical-fiber structure; applying the first laser beam from the optical-fiber structure onto a location on the tissue for stimulation of the tissue; and obtaining user input and based on the user input, controlling the first laser beam.

In some embodiments, the first laser beam has an infrared (IR) wavelength.

In some embodiments, the tissue is muscle tissue, and the action potential is a muscle action potential.

In some embodiments, the tissue is neural tissue, and the action potential is a nerve action potential.

Some embodiments further include obtaining a second laser beam having a second wavelength that is capable of directly stimulating muscle tissue, wherein the second wavelength is different than the first wavelength and has a different penetration depth into a given tissue; transmitting the second laser beam in the optical-fiber structure; applying light at the first wavelength to achieve a first tissue-penetration depth; and applying light at the second wavelength to achieve a second tissue-penetration depth.

Some embodiments further include obtaining a second laser beam having a second wavelength that is capable of directly stimulating muscle tissue, wherein the second wavelength is different than the first wavelength and has a different penetration depth into a given tissue; transmitting the second laser beam in the optical-fiber structure; and applying variable amounts of the first and second different wavelengths simultaneously to achieve a tissue-penetration depth that is variable based on the intensities of the first and second wavelengths of light.

Some embodiments further include obtaining a third light beam having a visible-light wavelength; transmitting the third light beam in the optical-fiber structure; and imaging the third light beam from the optical-fiber structure as an indication of where the first laser beam is directed.

Some embodiments further include providing a handpiece for manually directing the location of the imaged stimulation light; and covering at least a portion of the handpiece with a sterile cover.

In some embodiments, the obtaining user input includes coupling a control mechanism to a laser controller controlling the first laser diode in order to control a function of the controller, wherein the control mechanism is configured to be operated in conjunction with the handpiece.

In some embodiments, the control mechanism is mounted on the handpiece, and the obtaining user input includes coupling a manual operation of the control mechanism by a user to control the first laser beam.

Some embodiments further include providing a handpiece for manually directing the location of imaged stimulation light, wherein the obtaining user input includes coupling a user-operated control mechanism to a laser controller to control a function of the controller, wherein the control mechanism is separate from the handpiece and is configured to be operated such that operation of the control mechanism is independent of movement of the handpiece.

Some embodiments further include providing a light-delivery unit for directing the location of the imaged stimulation light, wherein the light-delivery unit includes a frame configured to be affixed to the subject, and a moveable light-delivery head connected to the frame; and positioning the light-delivery head to deliver light to one of a plurality of locations on the subject.

Some embodiments of the present invention include an apparatus that includes means for generating a first laser beam having a first wavelength that is capable of directly stimulating an action potential in muscle tissue of a subject, wherein light of the first wavelength has a first tissue-penetration profile; means for transmitting the first laser beam; means for imaging the transmitted first laser beam onto a location on the muscle tissue for stimulation of the action potential in the muscle tissue; and means for obtaining user input and based on the user input, controlling the first laser beam.

In some embodiments, the means for generating the first laser beam includes a laser diode and means for controlling electrical power to the laser diode to control timing and intensity of the first laser beam.

Some embodiments further include means for visibly indicating a location on the subject to which optical muscle stimulation is to be obtained by application of the first laser beam.

Some embodiments further include means for generating a second laser beam having a second wavelength that is capable of directly stimulating muscle tissue of a subject, wherein light of the second wavelength has a second tissue-penetration profile different than the first tissue-penetration profile, and wherein the means for generating the second laser beam is optically coupled to the means for imaging.

Some embodiments further include means for generating a third laser beam that is capable of optically cutting tissue, wherein the means for generating the third laser beam is optically coupled to the means for imaging.

In some embodiments, the means are compatible with use within a magnetic field of an operating magnetic resonance imaging (MRI) apparatus.

Some embodiments of the present invention include an apparatus that includes an elongated endoscope structure having an image-obtaining end configured to be inserted into a small opening in a subject to enable viewing of an interior tissue of the subject; a first laser diode operable to output a laser beam having a first wavelength, and that is capable of directly stimulating muscle tissue of a subject, wherein light of the first wavelength has a first tissue-penetration profile; a fiber holder operable to hold an optical fiber, the optical fiber having a first end configured to be optically coupled to receive the laser beam from the first laser diode and configured to deliver the laser beam to a second end to stimulate neural tissue of the viewed interior tissue of the subject; and a user-input interface operable to obtain user input and based on the user input, to control application of the first laser beam. Some embodiments further include the optical fiber.

In some embodiments, the fiber holder is further configured to implant and release the optical fiber in the subject.

In some embodiments, a high-power diode laser array is used for one or more of the light sources used in the above-described embodiments. For example, some embodiments use high-power MQW (multiple quantum well) multiple-emitter laser arrays available from Princeton Lightwave Inc., 2555 Route 130 South Suite 1, Cranbury, N.J. 08512, whose laser arrays output laser light with up to 30 watts or more power at 1.45 to 1.55 microns and up to 12 watts or more power at 1.85 microns. In some embodiments, the present invention uses lasers such as described in "218 W quasi-CW operation of 1.83 microns (i.e., micrometers) two-dimensional laser diode array" by M. Maiorov et al., *Electronics Letters*, Vol.35 No.8, 15 Apr. 1999. Some embodiments use the structures described for such lasers modified to produce other IR wavelengths. In some embodiments, the present invention uses light sources such as described in US Pat. No. 6,639,930 titled "Multi-level closed loop resonators and method for fabricating same" which issued Oct. 28, 2003; U.S. Pat. No. 6,556,611 titled "Wide stripe distributed Bragg reflector lasers with improved angular and spectral characteristics" which issued Apr. 29, 2003; U.S. Pat. No. 6,459,715 titled "Master-oscillator grating coupled power amplifier with angled amplifier section" which issued Oct. 1, 2002; U.S. Pat. No. 6,417,524 titled "Light emitting semiconductor device" which issued Jul. 9, 2002; U.S. Pat. No. 6,363,188 titled "Mode expander with co-directional grating" which issued Mar. 26, 2002; U.S. Pat. No. 6,339,606 titled "High power semiconductor light source" which issued Jan. 15, 2002; U.S. Pat. No. 6,301,279 titled "Semiconductor diode lasers with thermal sensor control of the active region temperature" which issued Oct. 9, 2001; and U.S. Pat. No. 6,184,542 titled "Superluminescent diode and optical amplifier with extended bandwidth " which issued Feb. 6, 2001; each of which is incorporated by reference.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
   a nerve-stimulation-and-surgical unit, the nerve-stimulation-and-surgical unit including:

a first nerve-stimulation-light-emitting source that is operative to emit a first nerve-stimulation infrared optical signal at a first wavelength;

a visible-light-emitting source operative to emit a visible optical pointer signal at a second wavelength that is visible to a human and that is different than the first wavelength and that is configured to indicate a location of the first nerve-stimulation infrared optical signal;

a tissue-ablation laser source that selectively delivers a surgical pulse of optical energy that ablates animal tissue;

a beam-combining unit located in the nerve-stimulation-and-surgical unit and operatively coupled to receive the first nerve-stimulation infrared optical signal from the first nerve-stimulation-light-emitting source, the visible optical pointer signal from the visible-light-emitting source, and the surgical pulse of optical energy from the tissue-ablation laser source, and to combine and output a single combined beam containing, the first nerve-stimulation infrared optical signal from the first nerve-stimulation-light-emitting source, the visible optical pointer signal from the visible-light-emitting source, and the surgical pulse of optical energy from the tissue-ablation laser source;

an optical-delivery element located at a delivery tip of the nerve-stimulation-and-surgical unit, wherein the optical-delivery element delivers the single combined beam through the delivery tip and focuses the single combined beam onto a nerve of a subject such that the focused beam triggers a nerve-action potential response in the nerve;

a nerve-response sensor operatively coupled to the nerve-stimulation-and-surgical unit, wherein the sensor senses a nerve response of the subject and generates signal information based on the nerve response; and control circuitry that is operatively coupled to control the first nerve-stimulation-light-emitting source, the visible-light emitting source, and the tissue-ablation laser source.

2. The apparatus of claim 1, the nerve-stimulation-and-surgical unit further comprising:

a second nerve-stimulation-light-emitting source that emits a third wavelength that directly stimulates a nerve, wherein the third wavelength is different than the first wavelength and has a different penetration depth into a given tissue than the first wavelength, and wherein light at the first wavelength is applied to achieve a first tissue-penetration depth, and light at the third wavelength is applied to achieve a second tissue-penetration depth that is different than the first tissue-penetration depth.

3. The apparatus of claim 1, further comprising:

a surgical-operation-suppression-signal generator operatively coupled to receive the signal information from the nerve-response sensor and, based on the received signal information, to generate a suppression signal for suppressing a surgical operation.

4. The apparatus of claim 3, wherein the tissue-ablation laser source is operable to deliver a surgical pulse of infrared (IR) optical energy that ablates animal tissue, and wherein the suppression signal variably reduces the surgical pulse.

5. The apparatus of claim 3, wherein the suppression signal inhibits the surgical pulse.

6. The apparatus of claim 3, wherein the suppression signal variably reduces the surgical pulse.

7. The apparatus of claim 1, wherein the beam-combining unit includes a first dichroic mirror that transmits one of the first wavelength and the second wavelength and reflects another one of the first wavelength and the second wavelength.

8. The apparatus of claim 1, wherein the beam-combining unit includes a first dichroic mirror and a second dichroic mirror.

9. The apparatus of claim 1, wherein the optical-focus element focuses to an area sufficiently small to stimulate a subset of just one or more nerves within a nerve bundle without stimulating at least another subset of the nerves in the nerve bundle.

10. The apparatus of claim 1, wherein the nerve-response sensor is located at a place other than the location of the single combined beam.

11. The apparatus of claim 1, further comprising a liquid-delivery unit configured to deliver, at the delivery tip, a liquid to the nerve of the subject.

12. The apparatus of claim 1, further comprising a focus plate at the delivery tip having a thickness such that light of the single combined beam comes to a focus at a surface of the focus plate.

13. The apparatus of claim 1, wherein the subject is a human subject and wherein the surgical pulse is configured to ablate tissue of the human subject at the focus location.

14. The apparatus of claim 1, wherein the subject is a human subject and wherein the surgical pulse is configured to cauterize tissue of the human subject at the focus location.

15. A method comprising:

providing a nerve-stimulation-and-surgical unit, the nerve-stimulation-and-surgical unit having a delivery tip, a first nerve-stimulation-light-emitting source, a second light-emitting source, and a third light-emitting source mounted in the nerve-stimulation-and-surgical unit and optics capable of combining three light signals;

obtaining, from the first nerve-stimulation-light-emitting source, a first infrared laser beam having a first wavelength that directly optically stimulates an action potential in a neural tissue of an animal subject;

obtaining user input and based on the user input, controlling the first infrared laser beam to form a optical stimulation signal;

emitting, from the second light-emitting source, a visible optical pointer signal at a second wavelength that is visible to a human, that is different than the first wavelength, and that is configured to indicate a location of the optical stimulation signal;

emitting, from the third light-emitting source, a surgical laser pulse that is configured to ablate tissue of the animal subject;

beam combining, with the optics, the first infrared laser beam, the visible optical pointer signal, and the surgical laser pulse into a single combined beam within the nerve-stimulation-and-surgical unit;

applying the single combined beam from the nerve-stimulation-and-surgical unit onto the location on the tissue for stimulation of the tissue, wherein the applying includes focusing the single combined beam through the delivery tip such that the focused single combined beam triggers a nerve-action potential response in the neural tissue;

sensing a nerve-response of the animal subject; and controlling an operation of the nerve-stimulation-and-surgical unit based on the sensed nerve response.

16. The method of claim 15, further comprising:
emitting a third wavelength that directly stimulates a nerve, wherein the third wavelength is different than the first wavelength and has a different penetration depth into a given tissue than the first wavelength, and wherein light at the first wavelength is applied to achieve a first tissue-penetration depth, and light at the third wavelength is applied to achieve a second tissue-penetration depth.

17. The method of claim 15, further comprising:
generating signal information based on the sensed nerve response; and
suppressing a surgical operation based on the signal information from the sensed nerve response.

18. The method of claim 17, wherein the surgical operation comprises an infrared (IR) surgical laser pulse, the method further comprising:
ablating animal tissue using the IR surgical laser pulse, wherein the suppressing inhibits the IR surgical laser pulse.

19. The method of claim 17, wherein the surgical operation comprises the surgical laser pulse, the method further comprising:
ablating animal tissue of the animal subject using the surgical laser pulse, wherein the suppressing inhibits the surgical laser pulse.

20. The method of claim 17, wherein the surgical operation comprises the surgical laser pulse, the method further comprising:
ablating animal tissue of the animal subject using the surgical laser pulse, wherein the suppressing variably reduces the surgical laser pulse.

21. The method of claim 15,
wherein the beam combining includes transmitting light of one of the first wavelength and the second wavelength and reflecting light of another one of the first wavelength and the second wavelength.

22. The method of claim 15, further comprising:
dichroic beam combining, into the single combined beam, the optical stimulation signal from the first light-emitting source, the first optical pointer from the second light-emitting source, and the surgical laser pulse.

23. The method of claim 15, wherein the focusing of the optical stimulation signal further includes focusing to an area sufficiently small to stimulate a subset of just one or more nerves within a nerve bundle without stimulating at least another subset of the nerves in the nerve bundle.

24. The method of claim 15, wherein the sensing of the nerve-response is done at a place other than the location of the single combined beam.

25. The method of claim 15, the method further comprising:
ablating tissue of the animal with the surgical laser pulse.

26. The method of claim 15, the method further comprising:
cauterizing tissue of the animal with the surgical laser pulse.

27. An apparatus comprising:
a nerve-stimulation-and-surgical unit, wherein the nerve-stimulation-and-surgical unit includes a delivery tip;
means for stimulating an action potential in a neural tissue of an animal, wherein the means for stimulating includes, a first infrared laser beam having a first wavelength that directly optically stimulates the action potential in the neural tissue of the animal;
means for obtaining user input and based on the user input, controlling the first laser beam;
means for emitting a visible optical pointer signal;
means for emitting an optical signal for removing tissue to effect optical-beam surgery;
means for beam combining the first infrared laser beam, the visible optical pointer signal and the optical signal for removing tissue into a single combined beam;
means for applying and focusing the first infrared laser beam of the single combined beam through the delivery tip of the nerve-stimulation-and-surgical unit onto a location on the neural tissue for stimulation of a nerve-action potential in the neural tissue, wherein the visible optical pointer signal of the single combined beam indicates the location of the first focused infrared laser beam on the neural tissue;
means for sensing a nerve-response of the subject; and
means for controlling an operation of the nerve-stimulation-and-surgical unit based on the sensed nerve response.

28. The apparatus of claim 27, further comprising:
means for suppressing operation of the means for emitting the optical signal for removing tissue.

29. An apparatus comprising:
a light-delivery handpiece of such small size to be readily hand held by a human user, the handpiece including:
a self-contained power source;
a first infrared-light-emitting source that is powered from the self-contained power source and is operative to emit a first infrared optical signal at a first wavelength;
a visible-light-emitting source operative to emit a visible optical pointer signal at a second wavelength that is visible to a human and that is different than the first wavelength and that is configured to indicate a focus location of the first infrared optical signal;
a tissue-ablation laser source operable to deliver a surgical pulse of optical energy that ablates animal tissue;
a beam-combining unit operatively coupled to receive the first infrared optical signal from the first infrared-light-emitting source, the visible optical pointer signal from the visible-light-emitting source, and the surgical pulse from the tissue-ablation laser source, and output a single combined beam containing the first infrared optical signal, the visible optical pointer signal from the visible-light-emitting source, and the surgical pulse;
an optical-delivery element located at a delivery tip of the handpiece, wherein the optical-delivery element delivers the single combined beam through the delivery tip onto the focus location on a human subject;
a nerve-response sensor operatively coupled to the handpiece, wherein the sensor senses a nerve response of the subject and generates signal information based on the nerve response that is coupled to control an operation of the handpiece;
a controller operatively coupled to control an operation of the apparatus.

30. The apparatus of claim 29, wherein the first infrared optical signal is pulsed and configured to cause a nerve-action potential in a nerve of the human subject at the focus location.

31. The apparatus of claim 29, wherein the surgical pulse is configured to ablate tissue of the human subject at the focus location.

32. The apparatus of claim 29, wherein the surgical pulse is configured to cauterize tissue of the human subject at the focus location.

33. The apparatus of claim 1, wherein the optical delivery element is affixed to a disposable plastic sheath, and wherein the optical delivery element includes a lens.

34. The apparatus of claim 1, wherein the nerve-stimulation-and-surgical unit includes a substantially in-line self-contained body, and wherein the nerve-stimulation-and-surgical unit further includes a self-contained power source located within the substantially in-line body.

* * * * *